(12) United States Patent
Fujita

(10) Patent No.: US 7,833,988 B2
(45) Date of Patent: Nov. 16, 2010

(54) GANKYRIN

(76) Inventor: Jun Fujita, Manhaimu Kamogawa 301, 14, Yoshidakawara-machi, Sakyo-ku, Kyoto-shi, Kyoto 606-8305 (JP)

( * ) Notice: Subject to any disclaimer, the term of this patent is extended or adjusted under 35 U.S.C. 154(b) by 0 days.

(21) Appl. No.: 11/083,944

(22) Filed: Mar. 21, 2005

(65) Prior Publication Data

US 2005/0170424 A1 Aug. 4, 2005

Related U.S. Application Data

(62) Division of application No. 09/509,775, filed as application No. PCT/JP98/04467 on Oct. 2, 1998, now abandoned.

(30) Foreign Application Priority Data

Oct. 3, 1997 (JP) ................................. 9-286214

(51) Int. Cl.
*A01N 43/04* (2006.01)
*A61K 31/70* (2006.01)
*C07H 19/00* (2006.01)
*C07H 21/00* (2006.01)

(52) U.S. Cl. .................... 514/44; 536/22.1; 536/24.1; 536/24.5; 536/23.5; 536/23.1

(58) Field of Classification Search ........................ None
See application file for complete search history.

(56) References Cited

FOREIGN PATENT DOCUMENTS

JP 9-075085 3/1997

OTHER PUBLICATIONS

Tamm et al., Lancet, Aug. 11, 2001;358(9280):489-97.*
Kawakami, et al. (2007) Nonviral Approaches for Targeted Delivery of Plasmid DNA and Oligonucleotide. J. Pharm. Sci., v.97(2):726-745.*
Baeuerle, et al., "Activation of DNA-Binding Activity in an Apparently Cytoplasmic Precursor of the NF$_\kappa$B Transcription Factor", *Cell*, 1988, vol. 53, No. 2, pp. 211-217.
Belghiti et al.; "Intrahepatic Recurrence After Resection of Hepatocellular Carcinoma Complicating Cirrhosis"; *Ann. Surg.*; 1991; vol. 214, No. 2; pp. 114-117.
Bowie et al., "Deciphering the Message in Protein Sequences Tolerance to Amino Acid Substitutions,", *Science*, 1990, vol. 247, pp. 1306-1310.
Burgess et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", *The Journal of Cell Biology*, 1990, vol. 111, pp. 2129-2138.
Calvet et al.; "Prognostic Factor of Hepatocellular Carcinoma in the West: A Multivariate Analysis in 206 Patients"; *Hepatology*; 1990; vol. 12, No. 4; pp. 753-760.
Database EMBL Online, Est., 495 bp, Aug. 27, 1996, Retrieved from EBI Database Accession No. AA035825, 2 Sheets, XP002238075.

Dawson et al., "The 26S-proteasome: regulation and substrate recognition" *Molecular Biology Reports*, 1997, vol. 24, No. 1-2, pp. 39-44.
Decaprio, et al., "The Product of the Retinoblastoma Susceptibility Gene has Properties of a Cell Cycle Regulatory Element", *Cell*, 1989, vol. 58, No. 6, pp. 1085-1095.
Demartino et al., "PA700, an ATP-dependent Activator of the 20 S Proteasome, Is an ATPase Containing Multiple Members of a Nucleotide-binding Protein Family.", *The Journal of Biological Chemistry*, Aug. 19, 1994, vol. 269, No. 33, pp. 20878-20884.
Franco et al.; "Resection of Hepatocellular Carcinomas"; *Gastroenterology*; 1990; vol. 98, No. 3; pp. 733-738.
Furutani et al.; "Decreased Expression and Rare Somatic Mutation of the CIPI/WAFI Gene in Human Hepatocellular Carcinoma"; *Cancer Letters*; 1997; vol. 111, pp. 191-197.
Furutani et al.; "Kan-1 (Bile Acid CoA:Amino Acid N-Acyltransferase) Messenger RNA as a Novel Predictive Indicator for Prognosis of Hepatocellular Carcinoma Patients After Partial Hepatectomy"; *Hepatology*, 1996; vol. 24, No. 6; pp. 1441-1445.
Higashitsuji et al., "Reduced stability of retinoblastoma protein by gankyrin, an oncogenic ankyrin-repeat protein overexpressed in hepatomas", *Nature Medicine*, Jan. 2000, vol. 6, No. 1, pp. 96-99.
Hori et al., "cDNA cloning and functional analysis of p28 (Nas6p) and p40.5 (Nas7p), two novel regulatory subunits of the 26S proteasome", *Gene*, Aug. 1988, vol. 216, No. 1, pp. 113-122.
Jamsa et al., "Structural Features of a Polypeptide Carrier Promoting Secretion of a β-Lactamase Fusion Protein in Yeast", *Yeast*, 1995, vol. 11, pp. 1381-1391.
Lambert et al., "cDNA sequence for human erythrocyte ankyrin", *Proc. Natl. Acad. Sci. USA*, Mar. 1990, vol. 87, pp. 1730-1734.
Lazar et al., "Transforming Growth Factor α: Mutation of Aspartic Acid 47 and Leucine 48 Results in Different Biological Activities", *Molecular and Cellular Biology*, 1988, vol. 8, No. 3, pp. 1247-1252.
Mise et al.; "Clinical Significance of Vascular Endothelial Growth Factor and Basic Fibroblast Growth Factor Gene Expression in Liver Tumor"; *Hepatology*; 1996; vol. 23, No. 3; pp. 455-464.
Thompson et al., "Convergence of Ets- and Notch-Related Structral Motifs in a Heteromeric DNA Binding Complex", *Sciences*, 1991, vol. 253, No. 5021, pp. 762-768.
Tobe et al.; "Prime Liver Cancer in Japan"; 1990; pp. 277-287.
Tobe et al.; "Prime Liver Cancer in Japan"; 1992; pp. 243-255.
Tobe et al.; "Prime Liver Cancer in Japan"; 1992; pp. 445-453.
Tobe et al.; Predictive Factors for Long Term Prognosis After Partial Hepatectomy for Patients With Hepatocellular Carcinoma in Japan; *Cancer*; 1994; vol. 74, No. 10; pp. 2772-2775.

(Continued)

*Primary Examiner*—Richard Schnizer
*Assistant Examiner*—Jennifer Pitrak
(74) *Attorney, Agent, or Firm*—Foley & Lardner LLP

(57) ABSTRACT

Gankyrin having the amino acid sequence as set forth in SEQ ID NO: 2, or modified gankyrin comprising an amino acid sequence modified by the deletion and/or addition of one or a plurality of amino acids and/or the substitution with other amino acids in the amino acid sequence of SEQ ID NO: 2 and retaining the biological activity of gankyrin, a gene encoding it, and a method of preparing said protein and uses thereof.

6 Claims, 11 Drawing Sheets

OTHER PUBLICATIONS

Wang et al., "A Single Nuclease Active Site of the *Escherichia coli* RecBCD Enzyme Catalyzes Single-stranded DNA Degradation in Both Directions", *The Journal of Biological Chemistry*, 2000, Vo. 275, No. 1, pp. 507-513.

Willardson et al., "Localization of the Ankyrin-binding Site on Erythrocyte Membrane Protein, Band 3", *J. Biol Chem.*, 1989, vol. 264, No. 27, pp. 15893-15899.

Zhang et al., "Expression and Functional Characterization of *Escherichia coli* NusA and Lambda Q as Glutathione S-Transferase Fusion Proteins", *Protein Expression and Purification*, 1995, vol. 6, pp. 625-631.

Lozano et al., "Gankyrin: An intriguing name for a novel regulator of p53 and RB," Cancer Cell, Jul. 3-4, 2005.

* cited by examiner

Fig.10
(A)
1  2  3  4
  — GANKYRIN
(B)
1  2  3  4  5
 ◄— GANKYRIN
(C)
1  2  3  4  5
 ◄— GANKYRIN Fig.11

Fig.13
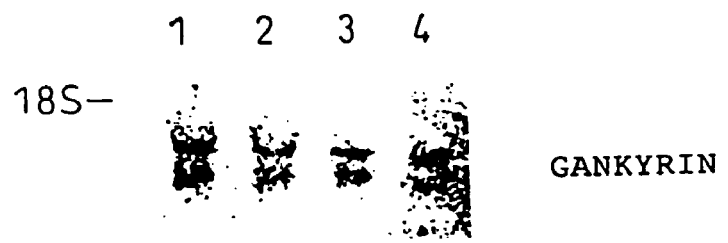
Fig.14
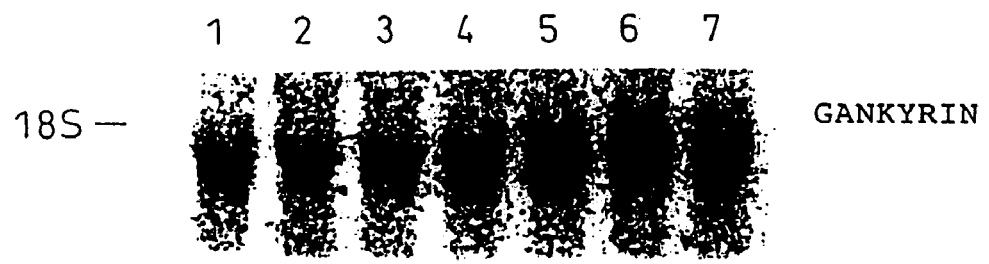

US 7,833,988 B2

GANKYRIN

This application is a divisional application of U.S. patent application Ser. No. 09/509,775, filed Mar. 31, 2000, which is the national stage application filed under 35 U.S.C. §371 of International Application No. PCT/JP98/04467, filed Oct. 2, 1998, which claims priority from Japanese patent application 9-286214, filed Oct. 3, 1997.

TECHNICAL FIELD

The present invention relates to a novel protein gankyrin, and to a method of preparation and to uses thereof.

BACKGROUND ART

Hepatocellular carcinoma (HCC) is one of the most prevalent cancers in the Orient and Southern Africa. In the past 10 years, there have been significant advances in the diagnosis and treatment of HCC patients, with a result that the cases of surgical treatment are increasing (Arii, S. et al., Primary liver cancer in Japan, Springer-Verlag (1992) 243-255; The Liver Cancer Study Group of Japan, Primary liver cancer in Japan, Springer-Verlag (1992) 445-453). Despite the marked progress, however, the survival rate remains low. One of the barriers to the lengthening of the survival period appears to be the occurrence of intrahepatic regeneration of the cancer after its complete removal on a macroscopic level (The Liver Cancer Study Group of Japan, Ann. Surg. (1990) 211, 277-287; Belghiti, J. et al., Ann. Surg. (1991) 214, 114-117).

In this connection, extensive efforts have been made to determine a prognosis judging factor that affects the intrahepatic regeneration and the lengthening of the survival period. Up to now, the inventor of the present invention has analyzed the expression of several genes of HCC (Mise, M. et al., Hepatology (1996) 23, 455-464; Furutani, M. et al., Hepatology (1996) 24, 1441-1445; Furutani, M. et al., Cancer Lett. (1997) 111, 191-197). As a result the present inventor has identified kan-1 (bile acid CoA: amino acid N-acyl transferase) mRNA as a novel prognosis judging factor. The expression of this factor is decreased in HCC with poor prognosis (Furutani, M. et al., Hepatology (1996) 24, 1441-1445).

In addition to the above, novel molecular markers of HCC, that add to the predicative value to conventional clinical prognostic factors such as portal complications, α-fetoprotein (AFP) levels, tumor size, the number of tumors, and the like, are sought (The Liver Cancer Study Group of Japan, Primary liver cancer in Japan, Springer-Verlag (1992) 445-453; The Liver Cancer Study Group of Japan, Ann. Surg. (1990) 211, 277-287; The Liver Cancer Study Group of Japan, Cancer (1994) 74, 2772-2780; Franco, D. et al., Gastroenterology (1990) 98, 733-738; Calvet, X. et al., Hepatology (1990) 12, 753-760).

DISCLOSURE OF THE INVENTION

In order to identify a molecular marker that is elevated in HCC, the inventor of the present invention has subtracted cDNA derived from the non-cancerous portion of the liver from cDNA made from HCC of the same patient. As a result, the inventors have isolated a novel gene, gankyrin, that consists of the ankyrin repeat motif alone and that exhibits carcinogenicity in in vitro and in in vivo assay systems.

Thus, the present invention provides a novel gankyrin polypeptide, genes encoding it, a method of preparing said polypeptide, an antibody against said polypeptide, and uses thereof.

In order to solve the above problems, the present invention provides a polypeptide comprising an amino acid sequence from Ala at position 14 to Gly at position 226 of SEQ ID NO: 2 and having the biological activity of gankyrin.

The present invention also provides a polypeptide comprising an amino acid sequence modified by the deletion and/or addition of one or a plurality of amino acids and/or the substitution with other amino acids, in the amino acid sequence from Ala at position 14 to Gly at position 226 of SEQ ID NO: 2 and retaining the biological activity of gankyrin.

The present invention also provides a polypeptide comprising an amino acid sequence from Met at position 1 to Gly at position 226 of SEQ ID NO: 2 and having the biological activity of gankyrin.

The present invention also provides a polypeptide comprising an amino acid sequence modified by the deletion and/or addition of one or a plurality of amino acids and/or the substitution with other amino acids in the amino acid sequence from Met at position 1 to Gly at position 226 in SEQ ID NO: 2 and retaining the biological activity of gankyrin.

The present invention also provides a polypeptide that is encoded by a DNA capable of hybridizing under a stringent condition to a DNA having the nucleotide sequence as set forth in SEQ ID NO: 1 and that has the biological properties of gankyrin. The stringent condition as used herein means, for example, a condition provided by 65° C. in 0.1×SSC and 0.1% SDS.

The present invention also provides a signal-added polypeptide, in which a signal sequence has been added to a polypeptide encoded by a DNA that encodes a polypeptide comprising an amino acid sequence from Ala at position 14 to Gly at position 226 of SEQ ID NO: 2 and having the biological activity of gankyrin, a DNA that encodes a polypeptide comprising an amino acid sequence modified by the deletion and/or addition of one or a plurality of amino acids and/or the substitution with other amino acids in the amino acid sequence from Ala at position 14 to Gly at position 226 of SEQ ID NO: 2 and retaining the biological activity of gankyrin, or a DNA capable of hybridizing under a stringent condition to a DNA that encodes a polypeptide having the nucleotide sequence as set forth in SEQ ID NO: 1 and having the biological properties of gankyrin. The stringent condition as used herein means, for example, a condition provided by 65° C. in 0.1×SSC and 0.1% SDS.

The present invention also provides a polypeptide comprising an amino acid sequence from Ala at position 14 to Met at position 231 of SEQ ID NO: 4 and having the biological activity of gankyrin.

The present invention also provides a polypeptide comprising an amino acid sequence modified by the deletion and/or addition of one or a plurality of amino acids and/or the substitution with other amino acids in the amino acid sequence from Ala at position 14 to Met at position 231 of SEQ ID NO: 4 and retaining the biological activity of gankyrin.

The present invention also provides a polypeptide comprising an amino acid sequence from Met at position 1 to Met at position 231 of SEQ ID NO: 4 and having the biological activity of gankyrin.

The present invention also provides a polypeptide comprising an amino acid sequence modified by the deletion and/or addition of one or a plurality of amino acids and/or the substitution with other amino acids in the amino acid sequence from Met at position 1 to Met at position 231 of SEQ ID NO: 4 and retaining the biological activity of gankyrin.

The present invention also provides a polypeptide that is encoded by a DNA capable of hybridizing under a stringent condition to a DNA having the nucleotide sequence as set forth in SEQ ID NO: 3 and that has the biological properties of gankyrin. The stringent condition as used herein means, for example, a condition provided by 65° C. in 0.1×SSC and 0.1% SDS.

The present invention also provides a signal-added polypeptide, in which a signal sequence has been added to a polypeptide encoded by a DNA that encodes a polypeptide comprising an amino acid sequence from Ala at position 14 to Met at position 231 of SEQ ID NO: 4 and having the biological activity of gankyrin, a DNA that encodes a polypeptide comprising an amino acid sequence modified by the deletion and/or addition of one or a plurality of amino acids and/or the substitution with other amino acids in the amino acid sequence from Ala at position 14 to Met at position 231 of SEQ ID NO: 4 and retaining the biological activity of gankyrin, or a DNA capable of hybridizing under a stringent condition to a DNA that encodes a polypeptide having the base sequence as set forth in SEQ ID NO: 3 and having the biological properties of gankyrin. The stringent condition as used herein means, for example, a condition provided by 65° C. in 0.1×SSC and 0.1% SDS.

The present invention also provides a polypeptide comprising an amino acid sequence from Ala at position 14 to Met at position 231 of SEQ ID NO: 6 and having the biological activity of gankyrin.

The present invention also provides a polypeptide comprising an amino acid sequence modified by the deletion and/or addition of one or a plurality of amino acids and/or the substitution with other amino acids in the amino acid sequence from Ala at position 14 to Met at position 231 of SEQ ID NO: 6 and retaining the biological activity of gankyrin.

The present invention also provides a polypeptide comprising an amino acid sequence from Met at position 1 to Met at position 231 of SEQ ID NO: 6 and having the biological activity of gankyrin.

The present invention also provides a polypeptide comprising an amino acid sequence modified by the deletion and/or addition of one or a plurality of amino acids and/or the substitution with other amino acids in the amino acid sequence from Met at position 1 to Met at position 231 of SEQ ID NO: 6 and retaining the biological activity of gankyrin.

The present invention also provides a polypeptide that is encoded by a DNA capable of hybridizing under a stringent condition to a DNA having the nucleotide sequence as set forth in SEQ ID NO: 5 and that has the biological properties of gankyrin. The stringent condition as used herein means, for example, a condition provided by 65° C. in 0.1×SSC and 0.1% SDS.

The present invention also provides a signal-added polypeptide, in which a signal sequence has been added to a polypeptide encoded by a DNA that encodes a polypeptide comprising an amino acid sequence from Ala at position 14 to Met at position 231 of SEQ ID NO: 6 and having the biological activity of gankyrin, a DNA that encodes a polypeptide comprising an amino acid sequence modified by the deletion and/or addition of one or a plurality of amino acids and/or the substitution with other amino acids in the amino acid sequence from Ala at position 14 to Met at position 231 of SEQ ID NO: 6 and retaining the biological activity of gankyrin, or a DNA capable of hybridizing under a stringent condition to a DNA that encodes a polypeptide having the base sequence as set forth in SEQ ID NO: 5 and having the biological properties of gankyrin. The stringent condition as used herein means, for example, a condition provided by 65° C. in 0.1×SSC and 0.1% SDS.

The present invention also provides a fusion polypeptide comprising the above polypeptide and another peptide or polypeptide.

The present invention also provides a DNA encoding the above polypeptide.

The present invention also provides a vector comprising the above DNA.

The present invention also provides a host transformed with the above vector.

The present invention also provides a method of preparing the above polypeptide, said method comprising culturing a host transformed with an expression vector comprising a DNA encoding said polypeptide and recovering the desired polypeptide from said culture.

The present invention also provides an antibody that specifically reacts to the above polypeptide. The antibody is preferably a monoclonal antibody or a polyclonal antibody.

The present invention also provides a method of detecting or determining a gankyrin polypeptide, said method comprising contacting the above antibody to a sample expected to contain said gankyrin polypeptide and detecting or determining the formation of an immune complex between said antibody and said gankyrin polypeptide.

The present invention also provides an antisense oligonucleotide that hybridizes any of the sites of the nucleotide sequence as set forth in SEQ ID NO: 1.

The present invention also provides an antisense oligonucleotide to at least 20 contiguous nucleotides in the nucleotide sequence as set forth in SEQ ID NO: 1. Said antisense oligonucleotide to the at least 20 contiguous nucleotides preferably have a translation initiation codon.

The present invention also provides an expression inhibitor of a gankyrin polypeptide, said inhibitor comprising said antisense oligonucleotide as an active ingredient.

The present invention also provides a method of screening an agonist or an antagonist of the gankyrin polypeptide to the binding of the gankyrin polypeptide and Rb, said method comprising contacting a gankyrin polypeptide or a substance containing the gankyrin polypeptide with a sample expected to contain the agonist or the antagonist of the gankyrin polypeptide in the presence of Rb, and detecting a free gankyrin polypeptide or Rb. The above substance containing the gankyrin polypeptide is for example a cell lysate that expresses gankyrin.

The present invention also provides a method of screening an agonist or an antagonist of the gankyrin polypeptide to the binding of the gankyrin polypeptide and NFκB, said method comprising contacting a gankyrin polypeptide or a material containing the gankyrin polypeptide with a sample expected to contain the agonist or the antagonist of the gankyrin polypeptide in the presence of NFκB, and detecting a free gankyrin polypeptide or NFκB. The above substance containing the gankyrin polypeptide is for example a cell lysate that expresses gankyrin.

BRIEF EXPLANATION OF DRAWINGS

FIG. 10 is an electrophoregram showing the result that fusion polypeptides of gankyrin polypeptides and HA were expressed in the 293 cells, immunoprecipitated and then were detected using various antibodies.

FIG. 11 is an electrophoregram showing the result that fusion polypeptides of gankyrin polypeptides and HA were expressed in the 293 cells, immunoprecipitated and then were detected, using various antibodies.

FIG. 13 is an electrophoregram showing the result that mRNAs in the NIH/3T3 cells propagated at various concentrations were detected in a similar manner to FIG. 12.

FIG. 14 is an electrophoregram showing the result that mRNAs in the hepatic tissue during the process of liver regeneration after partial hepatic resection in mice were detected in a similar manner to FIG. 12.

EMBODIMENT FOR CARRYING OUT THE INVENTION

Figure 1:
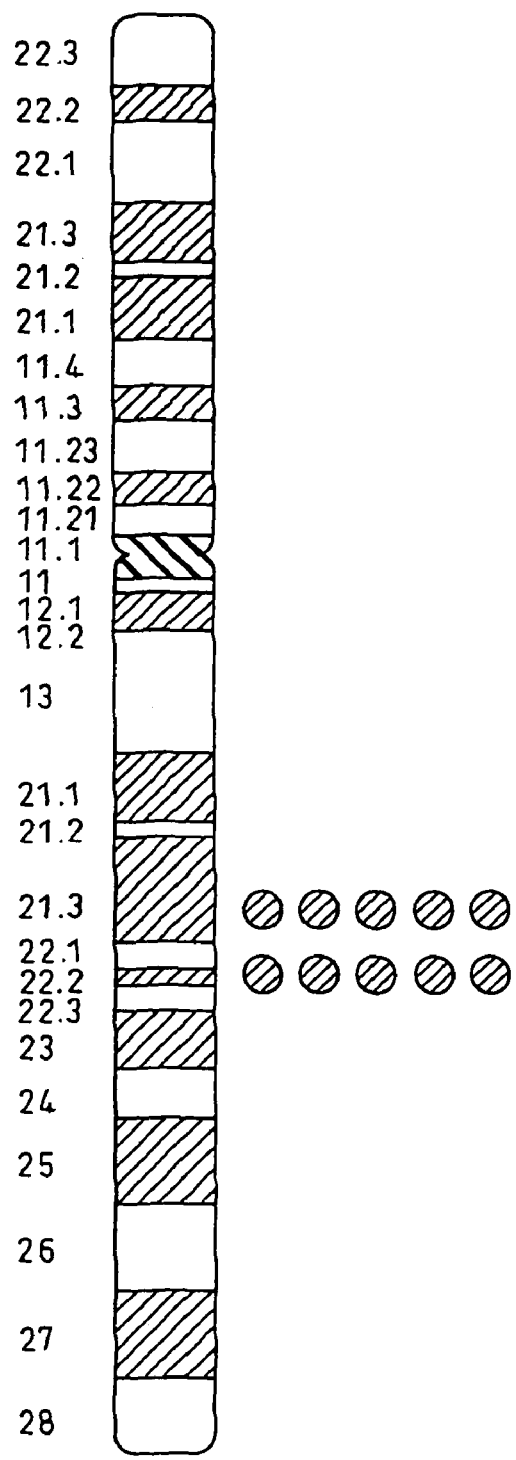
FIG. 1 is a diagram showing the position of a gankyrin gene on the human X chromosome.

In accordance with the present invention, a gankyrin polypeptide means a polypeptide having the biological activity of gankyrin. The biological activity of gankyrin is carcinogenicity, of which specific effects include, as described in Example 4, the elevation of colony-forming ability of cells in soft agar and the induction of tumorigenicity and the suppression of apoptosis in mice.

The gankyrin gene of the present invention and the cDNA thereof can be obtained by screening hepatic cancer cells or hepatic cancer tissue as its source to obtain the gene or the cDNA thereof. As a method of screening or isolating the gene or cDNA thereof, there can be used one that can selectively screen the gene whose amount expressed varies, such as the subtraction method (Nucleic Acids Research (1988) 16, 10937) and the differential hybridization method (Cell (1979) 16, 443-452).

The gene encoding the gankyrin polypeptide of the present invention can be obtained by the subtraction between a cDNA library prepared from the normal liver tissue and a cDNA library prepared from the hepatic cancer tissue to select cDNA derived from mRNA that is expressed in the hepatic cancer tissue but not in the normal liver tissue.

For example, in the subtraction method, cDNA obtained from the hepatic cancer tissue or the normal liver tissue is amplified. Primers to amplify the normal liver tissue are labeled with a labeling compound, for example biotin. Then, an excessive amount of double stranded cDNA derived from the normal liver tissue is mixed with a small amount of double stranded cDNA derived from the hepatic cancer tissue to form a mixture, which is then made single-stranded by heat denaturation, and then returned to double strands. Among the cDNA derived from hepatic cancer tissue, most of those that were also present in the normal liver tissue come to form double strands with the cDNA derived from the normal liver tissue and to be labeled.

However, when cDNAs derived from the hepatic cancer tissue form double strands with each other, they are not labeled. Accordingly, by removing cDNA double stranded DNA having a label, cDNA that is specific for the hepatic cancer tissue can be obtained. By repeating this procedure, cDNAs specific for the hepatic cancer tissue can be concentrated. The specific procedure is shown in Example 1. By using cDNA fragments or full-length cDNAs obtained as probes, it is also possible to conduct Northern blotting on mRNA from cells or tissues that express gankyrin polypeptides or from cells or tissues that do not express gankyrin polypeptides and thereby to confirm that the selected gene specifically expresses mRNA.

By screening cDNA libraries using cDNA or cDNA fragments obtained as above, it is possible to obtain gankyrin genes from different cells, tissues, organs or species. Furthermore, by determining the nucleotide sequence of the cDNA obtained, it is possible to determine the translation region that encodes a gankyrin gene product, a polypeptide, and thereby to obtain the amino acid sequence of this polypeptide. It is also possible to isolate chromosomal DNA by screening genomic DNA libraries using the obtained cDNA as a probe.

DNA libraries such as cDNA libraries or genomic DNA libraries may be prepared by a method described, for example, in Sambrook, J. et al., Molecular Cloning, Cold Spring Harbor Laboratory Press (1989), or commercially available DNA libraries may be used.

The gene or DNA of the present invention can be obtained by the PCR method using as a primer the nucleotide sequence or part thereof, if it is known.

The gankyrin polypeptide of the present invention includes a polypeptide that is encoded by a DNA that hybridizes to a nucleic acid having the nucleotide sequence as set forth in SEQ ID NO: 1 under a stringent condition, and that has the biological activity of gankyrin.

Such stringent conditions include, for example, a low stringent condition. By way of example, a low stringent condition is 50° C. in 2×SSC and 0.1% SDS. More preferably, there may be mentioned a high stringent condition. By way of example, a high stringent condition is 65° C. in 0.1×SSC and 0.1% SDS.

The above hybridizing DNA is preferably naturally occurring DNA, and, for example, it may be cDNA or genomic DNA. Homology search carried out on the amino acid sequence as set forth in SEQ ID NO: 2 and the nucleotide sequence as set forth in SEQ ID NO: 1 using all the sequences contained in the known DNA databases (GenBank, EMBL) and the protein database (SWISS-PLOT) did not give any matches. From this result, it was revealed that the gene and the gene product polypeptide of the present invention are novel molecules.

As shown in Example 1, it was found that the gene that hybridizes to the cDNA of the novel gankyrin polypeptide of the present invention is widespread in non-human animals such as rats, mice, and the like, and also in various tissues. Thus, the above naturally occurring DNA may be cDNA or genomic DNA derived from the tissues in which mRNA that hybridizes to cDNA of human gankyrin polypeptide in, for example, Example 1 is detected.

The present invention also encompasses a DNA that hybridizes to a nucleic acid having the nucleotide sequence as set forth in SEQ ID NO: 2 and that encodes a polypeptide having the activity of gankyrin. This DNA can also be expressed by the above-mentioned method. In order to obtain such a gankyrin polypeptide, synthetic oligonucleotide primers can be used to introduce the desired mutation in the nucleotide sequence of a gankyrin gene (Mark, D. F. et al., Proc. Natl. Acad. Sci. U.S.A. (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. U.S.A. (1982) 79, 6409-6413).

In addition to being cDNA and genomic DNA that encodes the gankyrin polypeptide, it may be a synthetic DNA. Specifically, there may be mentioned a DNA that encodes gankyrin having the amino acid sequence as set forth in SEQ ID NO: 2, and a DNA having the nucleotide sequence as set forth in SEQ ID NO: 1 is used. These DNAs may be produced using gene engineering technology that is known per se.

An obtained transformant *Escherichia coli* containing the plasmid pBS-t4-11 described hereinbelow in Example 1 was designated as *Escherichia coli* DH5α (pBS-t4-11) and was internationally deposited on Sep. 29, 1997, with the National Institute of Bioscience and Human-Technology, Agency of Industrial Science and Technology, MITI (Higashi 1-Chome 1-3, Tsukuba-shi, Ibaraki, Japan) under the accession numbers FERM BP-6128.

As the gankyrin polypeptide of the present invention, there can be mentioned a gankyrin polypeptide having an amino acid sequence that is identical or substantially identical to the amino acid sequence as set forth in SEQ ID NO: 2. Specifically, in addition to gankyrin having the amino acid sequence as set forth in SEQ ID NO: 2, there can be mentioned those in which one or more, preferably 2 or more and 30 or less, more preferably 2 or more and 10 or less amino acids are deleted, one or more, preferably 2 or more and 30 or less, more preferably 2 or more and 10 or less amino acids are added to the amino acid sequence as set forth in SEQ ID NO: 2; or one or more, preferably 2 or more and 30 or less, more preferably 2 or more and 10 or less amino acids in the amino acid sequence as set forth in SEQ ID NO: 2 are substituted with other amino acids.

The present invention also includes a polypeptide that has the biological activity of gankyrin and that is homologous to a polypeptide having the amino acid sequence as set forth in SEQ ID NO: 2. As used herein, "homologous polypeptides" refers to those polypeptides that have an amino acid homology of at least 70%, preferably at least 80%, more preferably at least 90%, and more preferably at least 95% or more, generally, for at least 20, preferably 30 contiguous amino acid residues to the amino acid sequence as set forth in SEQ ID NO: 2.

The gankyrin polypeptides of the present invention differ in amino acid sequence, molecular weight, isoelectric point, or presence or form of sugar chains, depending on the cells or host that produce the polypeptides, or methods of purification described hereinbelow. However, the gankyrin polypeptides obtained are included in the present invention as long as they have the activity substantially equivalent to that of a naturally occurring gankyrin polypeptide. As the activity that is substantially equivalent to the gankyrin polypeptide as used herein, there can be mentioned carcinogenicity as in Example 4 described below, such as the elevation of colony-forming ability of cells in soft agar and the suppression of tumorigenicity and of apoptosis induction in mice. Substantially equivalent as used herein means that carcinogenicity is equivalent in property.

As a partial peptide of the gankyrin polypeptide of the present invention, there can be mentioned, for example, a partial peptide comprising one or more than one region of the hydrophobic region or the hydrophilic region estimated from the hydrophobic plot analysis among the gankyrin molecules. These partial peptides can include part or all of a hydrophobic region or part or all of a hydrophilic region.

The partial peptide of the gankyrin polypeptide of the present invention can be produced according to the peptide synthesis method that is known per se or by cleaving the gankyrin polypeptide of the present invention with a suitable peptidase. The peptide synthesis method may be, for example, a solid phase synthesis or a liquid phase synthesis.

After the reaction, the partial peptide of the present invention can be isolated and purified by combining conventional purification methods such as solvent extraction, distilation, column chromatography, high performance liquid chromatography, and recrystalization.

The DNA constructed as described above can be expressed by a known method to obtain a gankyrin polypeptide. When mammalian cells are used, expression may be accomplished using an expression vector containing a commonly used useful promoter/enhancer, the gene to be expressed, and DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for expression of gankyrin polypeptide, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Nature (1979) 277, 108) when the SV40 promoter/enhancer is used, or by the method of Mizushima et al. (Nucleic Acids Res. (1990) 18, 5322) when the HEF1α promoter/enhancer is used.

In the case of *Escherichia coli* (*E. coli*), expression may be effected by operably linking a conventionally used useful promoter, a signal sequence for antibody secretion, and the antibody gene to be expressed, followed by expression thereof. As the promoter, for example, there can be mentioned the lacZ promoter and the araB promoter. The method of Ward et al. (Nature (1098) 341, 544-546; FASEB J. (1992) 6, 2422-2427) may be used when the lacZ promoter is used, and the method of Better et al. (Science (1988) 240, 1041-1043) may be used when the araB promoter is used.

As the signal sequence for gankyrin polypeptide secretion, when produced in the periplasm of *E. coli*, the pelB signal sequence (Lei, S. P. et al., J. Bacteriol. (1987) 169, 4379) can be used.

As the origin of replication, there can be used those derived from SV40, polyoma virus, adenovirus, bovine papilloma virus (BPV) and the like. Furthermore, for the amplification of gene copy number in the host cell system, expression vectors can include as selectable markers the aminoglycoside transferase (APH) gene, the thymidine kinase (TK) gene, *E. coli* xanthine guaninephosphoribosyl transferase (Ecogpt) gene, the dihydrofolate reductase (dhfr) gene and the like.

For the production of a gankyrin polypeptide, any production system can be used. The production system of gankyrin polypeptide preparation comprises the in vitro or the in vivo production system. As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells (J. Exp. Med. (1995) 108, 945), COS cells, myeloma cells, baby hamster kidney (BHK) cells, HeLa cells, and Vero cells, (2) amphibian cells such as *Xenopus oosytes* (Valle, et al., Nature (1981) 291, 358-340), or (3) insect cells such as sf9, sf21, and Tn5. As CHO cells, preferably dhfr-CHO (Proc. Natl. Acad. Sci. U.S.A. (1980) 77, 4216-4220) that lacks the DHFR gene and CHO K-1 (Proc. Natl. Acad. Sci. U.S.A. (1968) 60, 1275) may be used.

Known plant cells include, for example, those derived from *Nicotiana tabacum*, which is subjected to callus culture. Known fungal cells include yeasts such as the genus *Saccharomyces*, for example *Saccharomyces cereviceae*, or filamentous fungi such as the genus *Aspergillus*, for example *Aspergillus niger*.

When the prokaryotic cells are used, there are the production systems which employ bacterial cells. Known bacterial cells include *Escherichia coli* (*E. coli*), and *Bacillus subtilis*.

By transforming these cells with the desired DNA and culturing the transformed cells in vitro, the gankyrin polypeptide can be obtained. Culturing is carried out in a known method. For example, as the culture liquid, DMEM, MEM, RPMI1640, and IMDM can be used, and serum supplements such as fetal calf serum (FCS) may be used in combination, or serum-free culture medium may be used. pH during the culture is preferably about 6 to 8. The culturing is usually conducted at about 30 to 40° C. for about 15 to 200 hours with optional medium exchange, aeration and agitation.

As in vivo production systems, there can be mentioned those which employ animals and those which employ plants. The desired DNA is introduced into an animal or a plant, and the gankyrin polypeptide is produced in such an animal or a plant and then collected. As used herein "host" encompasses these animals and plants.

When animals are used, there are the production systems which employ mammals and insects.

As mammals, goats, pigs, sheep, mice, and cattle can be used (Vicki Glaser, SPECTRUM Biotechnology Applications, 1993). When mammals are used, transgenic animals can also be used.

For example, an desired DNA is inserted into the middle of the gene encoding protein which is inherently produced in the milk such as goat β casein to prepare fusion genes. DNA fragments containing the fusion gene into which said DNA has been inserted are injected into a goat embryo, and the embryo is introduced into a female goat. The gankyrin polypeptide is obtained from the milk produced by the transgenic goat born to the goat who received the embryo or offsprings thereof. In order to increase the amount of milk containing the gankyrin polypeptide produced by the transgenic goat, hormones may be given to the transgenic goat as appropriate (Ebert, K. M. et al., Bio/Technology (1994) 12, 699-702).

When insects are used, silkworms, for example, can be used. When silkworms are used, baculovirus into which the desired DNA has been inserted is infected to the silkworm, and the desired gankyrin polypeptide can be obtained from the body fluid of the silkworm (Susumu, M. et al., Nature (1985) 315, 592-594).

When plants are used, tabacco for example can be used. Moreover, when tabacco is used, the desired DNA is inserted into an expression vector for plants, for example PMON 530, and then the vector is introduced into a bacterium such as *Agrobacterium tumefaciens*. The bacterium is then infected to tabacco such as *Nicotiana tabacum* to obtain the desired polypeptide from the leaves of the tabacco (Julian, K.-C. Ma et al., Eur. J. Immunol. (1994) 24, 131-138). As methods of introducing an expression vector into a host, there can be used a known method such as the calcium phosphate method (Virolgoy (1973) 52, 456-467), the electroporation method (EMBO J. (1982) 1, 841-845), and the like. Considering the frequency of use of the host's codon for use in expression, a sequence having a better efficiency of expression can be designed (Grantham, R. et al., Nucleic Acids Research (1981) 9, r43-r74).

That the gankyrin gene products thus obtained have the biological activity of gankyrin can be confirmed, for example, in the following manner. Using, for example, a method described in Example 4 below, cells that produce a gankyrin polypeptide are cultured in soft agar. Gankyrin polypeptide-expressing cells have an elevated colony-forming ability in soft agar. Alternatively, cells that express a gankyrin polypeptide are grafted to mice. Cells that express a gankyrin polypeptide show an elevated tumorigenicity. Alternatively, cells that express a gankyrin polypeptide are placed under a apoptosis-inducing condition. Cells that express a gankyrin polypeptide suppress the induction of apoptosis.

Polypeptides obtained as described above can be isolated from the inside or outside of the host as a substantially pure homogeneous polypeptide. Separation and purification of the gankyrin polypeptide may be accomplished by, but this is not limited to, the separation and the purification methods conventionally used for protein purification. For example, the gankyrin polypeptide can be separated and purified by selecting and combining, as appropriate, methods including, but not limited to, chromatography columns, filtration, ultrafiltration, salting-out, solvent precipitation, immunoprecipitation, SDS-polyacrylamide gel electrophoresis, isoelectric focusing, dialysis, and the like.

As chromatography, there may be mentioned, for example, affinity chromatography, ion exchange chromatography, hydrophobic chromatography, gel-filtration, reverse phase chromatography, adsorption chromatography, and the like (Strategies for Protein Purification and Characterization: A Laboratory Course Manual. Ed Daniel R. Marshak et al., Cold Spring Harbor Laboratory Press, 1986). These chromatographies can be carried out using a liquid chromatography such as HPLC and FPLC. Before or after purification, gankyrin polypeptides may be modified by the action of a suitable protein-modifying enzyme, or peptides can partially be removed. As the protein-modifying enzymes, there may be used trypsin, chymotrypsin, lysil endopeptidase, protein kinase, glucosidase, and protein kinase, glucosidase.

The gankyrin polypeptide of the present invention is important since it is used in a screening method. Thus, it is important since it is used in a method of screening an agonist or an antagonist of the gankyrin polypeptide, said method comprising contacting a gankyrin polypeptide or a material containing the gankyrin polypeptide with a sample expected to contain an agonist or an antagonist of the gankyrin polypeptide in the presence of Rb, and detecting or determining a free gankyrin polypeptide or Rb; or a method of screening an agonist or an antagonist of the gankyrin polypeptide, said method comprising contacting a gankyrin polypeptide or a material containing the gankyrin polypeptide with a sample expected to contain the agonist or the antagonist of the gankyrin polypeptide in the presence of NFκB (Baeuerle, P. A. et al., Cell (1988) 53, 211-217), and detecting or determining a free gankyrin polypeptide or NFκB.

The gankyrin polypeptide for use in these screening methods may be either a recombinant type or a natural type. It may also be a partial peptide of the gankyrin polypeptide as long as it retains the property of binding to Rb or NFκB. As the substance containing the gankyrin polypeptide, there may be mentioned the lysates of the cells that express gankyrin polypeptides.

Thus, the present invention relates to a method of screening an agonist or an antagonist of the gankyrin polypeptide comprising comparing a free gankyrin polypeptide or Rb detected or determined when a gankyrin polypeptide or a material containing the gankyrin polypeptide and a sample expected to contain the agonist or the antagonist of the gankyrin polypeptide are contacted, and a free gankyrin polypeptide or Rb detected or determined when a gankyrin polypeptide or a material containing the gankyrin polypeptide and a sample that does not contain the agonist or the antagonist of the gankyrin polypeptide are contacted, both in the presence of Rb.

The present invention also relates to a method of screening an agonist or an antagonist of the gankyrin polypeptide comprising comparing a free gankyrin polypeptide or NFκB detected or determined when a gankyrin polypeptide or a material containing the gankyrin polypeptide and a sample expected to contain the agonist or the antagonist of the gankyrin polypeptide are contacted, and a free gankyrin polypeptide or NFκB deleted or determined when a gankyrin polypeptide or a substance containing the gankyrin polypeptide and a sample that does not contain the agonist or the antagonist of the gankyrin polypeptide are contacted, both in the presence of NFκB.

In order to detect or determine free gankyrin polypeptides, Rb or NFκB in these screening methods, gankyrin polypeptides, Rb or NFκB are labeled with, for example, biotin, avidin, a radioisotope such as $[^{125}I]$, $[^{35}S]$, $[^{3}H]$, $[^{14}C]$, a fluorescent substance, an enzyme such as horseradish peroxidase and alkaline phosphatase, and then the label is detected or determined. These labeling compounds are known and can be labeled by conventional methods. Free gankyrin polypeptides, Rb, or NFκB can also be detected or determined using antibodies to gankyrin polypeptides, Rb, or NFκB.

Specifically, a gankyrin polypeptide is bound to a support such as beads or a plate, to which a sample expected to contain an agonist or an antagonist of the gankyrin polypeptide is added in the presence of Rb or NFκB, and after incubation, Rb or NFκB contained in the solution may be detected or determined with an antibody. Alternatively, in order to detect or determine free RB or NFκB, Rb or NFκB that is bound to the gankyrin polypeptide immobilized on the plate may be detected or determined.

At this time, a fusion polypeptide in which a gankyrin polypeptide has been fused to another peptide or polypeptide through gene engineering technology may be used. Such another peptide or polypeptide that can be subjected to fusion include hemaglutinin (HA), FLAG, and the like, and a free gankyrin polypeptide can be detected or determined using antibodies to another peptide or polypeptide that are subjected to fusion. Thus, the fusion polypeptides in which a gankyrin polypeptide and another peptide or polypeptide have been fused through gene engineering technology are useful in the present invention.

Samples expected to contain an agonist or an antagonist for use in the screening method of the present invention include, for example, peptides, proteins, non-peptide compounds, synthetic compounds, microbial fermentation products, marine organism extracts, plant extracts, cell extracts, or animal cell extracts. These samples may be novel or known substances.

The screening method of the present invention is useful for detecting or determining an agonist or an antagonist having carcinogenicity.

It was found in the present invention that gankyrin polypeptides interact with Rb or NFκB. Since gankyrin polypeptides have tumorigenicity, agonists or antagonists of gankyrin polypeptides that modulate the binding of a gankyrin polypeptide and Rb or NFκB are useful as pharmaceuticals.

Specifically, in order to conduct the above-mentioned screening method, the gankyrin polypeptide of the present invention or a sample expected to contain the gankyrin polypeptide is first suspended in a buffer solution suitable for screening and then immobilized on a plate thereby to prepare a gankyrin polypeptide sample.

Any buffer solution may be used as long as it does not inhibit the binding of a gankyrin polypeptide and, for example, a phosphate buffer of pH 6 to 8, Tris-HCl buffer, PBS, and HBSS may be used. In order to reduce non-specific binding, it is also possible to add protein such as bovine serum albumin, a surfactant such as CHAPS, Tween 80, digitonin, and the like. Furthermore, in order to suppress the decomposition of the gankyrin polypeptide with proteolyltic enzymes, inhibitors of proteolytic enzymes such as PMSF, pepstatin, leupeptin, and the like can be added.

Then, to the gankyrin polypeptide sample are added Rb or NFκB that has been labeled with a radioisotope and an appropriate concentration of sample, which are reacted at about 0 to 50° C. (preferably about 4 to 37° C.) for about 0.5 to 24 hours (preferably about 0.5 to 3 hours). After the reaction, it is washed with an appropriate amount of buffer and the amount of radioactivity remaining in the gankyrin polypeptide sample is counted by a gamma counter or liquid scintillation counter. In order to determine non-specific binding at this time, another polypeptide that does not interact with the gankyrin polypeptide is similarly labeled and added to prepare a gankyrin polypeptide sample. The gankyrin polypeptide sample to which a buffer that does not contain the sample has been added is used as a negative control.

The amount of non-specific binding subtracted from the amount of remaining radioactivity give the amount of specific binding. A sample that reduces the specific binding as compared to the case when no sample was added to the reaction can be selected as a candidate substance for an agonist or an antagonist of the gankyrin polypeptide.

An agonist or an antagonist of the gankyrin polypeptide obtained by the screening method of the present invention can be applied to screening, for example, peptides, proteins, non-peptide compounds, synthetic compounds, microbial fermentation products, marine organism extracts, plant extracts, cell extracts, or animal cell extracts using the screening method. These samples may be novel or known substances.

An agonist or an antagonist of a gankyrin polypeptide is a substance that inhibits the binding of the gankyrin polypeptide and Rb or NFκB. Substances obtained by addition, deletion or substitution of part of the structure of an agonists or an antagonists of a gankyrin polypeptide obtained by the screening method of the present invention is also included into agonists or antagonists of gankyrin polypeptides obtained by the screening method of the present invention.

When agonists or antagonists of gankyrin polypeptides obtained by the screening method of the present invention are used as medicaments for humans and mammals such as mice, rats, guinea pigs, rabbits, chickens, cats, dogs, sheep, pigs, cattle, monkeys, baboons, and chimpanzees, they may be used in a conventional method.

For example, they may be used, as desired, orally as sugar-coated tablets, capsules, elixirs, and microcapsules, or parenterally in the form of sterile solutions with water or other pharmaceutically acceptable liquids or in the form of injections as suspensions. For example, agonists or antagonists of gankyrin polypeptides are produced in unit dosage forms required for generally accepted formulations by mixing with physiologically acceptable carriers, flavoring agents, excipients, vehicles, antiseptics, stabilizers, and binders. The amount of active ingredients in these formulations is designed to provide an indicated suitable range of doses.

Additives that can be blended into tablets and capsules include, for example, binders such as gelatin, corn starch, tragacanth, gum Arabic, excipients such as crystalline cellulose, swelling agents such as alginate, lubricating agents such as magnesium stearate, sweetening agents such as sucrose, lactose, and saccharin, and flavoring agents such as peppermint, Gaultheria adenothrix oil, or cherry. When the formulation unit form is a capsule, liquid carriers such as lipids can be included to the above materials. Sterile compositions for injection can be formulated according to the conventional formulation method for dissolving or suspending active substances in a vehicle such as distilled water for injection, and natural plant oils such as sesame oil and coconut oil.

As aqueous solutions for injection, there may be mentioned, for example, isotonic liquids such as physiological saline, glucose and other adjuvants such as D-sorbitol, D-mannose, D-mannitol, and sodium chloride, and they may be used in combination with suitable solubilizing agents such as alcohols, specifically ethanol, polyalchohols including, for example, propylene glycol and polyethylene glycol, nonionic surfactants such as polysorbate 80 (TM), and HCO-50.

An oily liquid includes, for example, sesame oil and soybean oil, which may be used together with solubilizing agents such as benzyl benzoate and benzyl alchohol. There may be also blended buffers such as phosphate buffer and sodium acetate buffer, analgesics such as benzalkonium chloride and procaine chloride, stabilizing agents such as benzyl alchohol and phenol, and antioxidants. Prepared injections are usually filled into suitable ampoules.

The dosage of agonists or antagonists of gankyrin polypeptides for a human adult (assuming the body weight of 60 kg) is, when given orally, usually about 0.1 to 100 mg/day, preferably about 1.0 to 50 mg/day, and more preferably about 1.0 to 20 mg/day, though this may vary depending on the medical conditions.

When given parenterally, the dose per administration for a human adult (assuming the body weight of 60 kg) of usually about 0.01 to 30 mg/day, preferably about 0.1 to 20 mg/day, and more preferably about 0.1 to 10 mg/day in the case of injections is conveniently administered via intravenous injection, though this may vary depending on the subject, subject organ, medical conditions, and the method of administration. For other animals also, the amount converted in terms of the body weight of 60 kg may be administered.

Anti-gankyrin polypeptide antibodies of the present invention can be obtained as monoclonal or polyclonal antibodies using known methods.

Monoclonal antibodies can be obtained by using a gankyrin polypeptide as a sensitizing antigen, which is immunized in a conventional method for immunization, by fusing the immune cells thus obtained with known parent cells, and screening monoclonal antibody-producing cells using a known screening method.

Specifically, monoclonal or polyclonal antibodies may be generated as follows.

For example, though the gankyrin polypeptide to be used as a sensitizing antigen for generation of antibodies is not limited by the animal species from which the antibodies are obtained, it is preferably derived from a mammal such as humans, mice, or rats. These gankyrin polypeptides derived from humans, mice, or rats can be obtained using the gene sequences disclosed in the present invention.

According to the present invention, gankyrin polypeptides that have the biological activity of all the gankyrin polypeptides disclosed in the present invention can be used as the gankyrin polypeptide for use as a sensitizing antigen. As fragments of gankyrin polypeptides, there may be mentioned, for example, C-terminal fragments of gankyrin polypeptides. As used herein "anti-gankyrin polypeptide antibody" means an antibody that specifically reacts to the full-length or fragments of a gankyrin polypeptide.

Genes encoding a gankyrin polypeptide or fragments thereof may be inserted to a known expression system to transform the host cell described herein, and the desired gankyrin or the fragments thereof are obtained by a known method from the inside or the outside of the host cell and then the gankyrin polypeptide may be used as a sensitizing antigen. Alternatively, cells that express gankyrin polypeptide or lysates thereof may be used as a sensitizing antigen.

Mammals to be immunized with the sensitizing antigen are not specifically limited, and they are preferably selected in consideration of their compatibility with the parent cell for use in cell fusion. They generally include rodents, lagomorphs, and primates.

Rodents include, for example, mice, rats, hamsters, and the like. Lagomorphs include, for example, rabbits. Primates include, for example, monkeys. As monkeys, catarrhines (Old-World monkeys) such as cynomolgi, rhesus monkeys, sacred baboons, chimpanzees etc. are used.

Immunization of animals with a sensitizing antigen is carried out using a known method. A general method, for example, involves the intraperitoneal or subcutaneous administration of a sensitizing antigen to the mammal. Specifically, a sensitizing antigen which has been diluted and suspended in an appropriate amount of phosphate buffered saline (PBS) or physiological saline etc. is mixed, as desired, with an appropriate amount of a common adjuvant, for example Freund's complete adjuvant. After being emulsified, it is preferably administered to the mammal for several times every 4 to 21 days. Alternatively a suitable carrier may be used at the time of immunization of the sensitizing antigen. After such immunization, the increase in the desired antibody levels in the serum is confirmed by a conventional method.

In order to obtain polyclonal antibodies to a gankyrin polypeptide, the blood of the mammal that was sensitized with the antigen is removed after the increase in the desired antibody levels in the serum has been confirmed. Serum is separated from the blood. As polyclonal antibodies, serum containing the polyclonal antibodies may be used, or, as desired, the fraction containing the polyclonal antibodies may be isolated from the serum.

In order to obtain monoclonal antibodies, immune cells of the mammal that was sensitized with the antigen are removed and are subjected to cell fusion after the increase in the desired antibody levels in the serum has been confirmed. At this time preferred immune cells that are subjected to cell fusion include, in particular, the spleen cells.

The mammalian myeloma cells as the other parent cells which are subjected to cell fusion with the above-mentioned immune cells preferably include various known cell lines such as P3 (P3X63Ag8.653) (Kearney, J. F. et al., J. Immunol. (1979) 123: 1548-1550), P3X63Ag8.U1 (Yelton, D. E., et al., Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), FO (de St. Groth, S. F. and Scheidegger, D., J. Immunol. Methods (1980) 35: 1-21), S194 (Trowbridge, I. S., J. Exp. Med. (1978) 148: 313-323), R210 (Galfre, G. et al., Nature (1979) 277: 131-133) and the like.

Cell fusion between the above immune cells and the myeloma cells may be essentially conducted in accordance with a known method such as is described in Milstein et al. (Kohler, G. and Milstein, C., Methods Enzymol. (1981) 73: 3-46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added, as desired, to enhance the efficiency of the fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture and, besides, a serum supplement such as fetal calf seran (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v), and mixed to obtain the desired fusion cells (hybridomas). Then, by repeating the sequential addition of a suitable culture liquid and centrifugation to remove the supernatant, cell fusion agents etc. which are undesirable for the growth of the hybridoma can be removed.

Said hybridoma is selected by culturing in a conventional selection medium, for example, the HAT culture medium (a culture liquid containing hypoxanthine, aminopterin, and thymidine). Culturing in said HAT culture medium is continued generally for a period of time sufficient to effect killing of the cells other than the desired hybridoma (non-fusion cells), generally several days to several weeks. Then, the conventional limiting dilution method is conducted in which the hybridomas that produce the desired antibody are screened and cloned.

In addition to obtaining the above hybridoma by immunizing an animal other than the human with an antigen, it is also possible to sensitize human lymphocytes infected with EB virus with a gankyrin polypeptide, cells expressing a gankyrin polypeptide, or their lysates in vitro, and to allow the resulting sensitized lymphocytes to be fused with a human-derived myeloma cell having a permanent division potential, for example U266, and thereby to obtain a hybridoma producing the desired human antibody having the activity of binding the gankyrin polypeptide (see Japanese Unexamined Patent Publication (Kokai) No. 63(1988)-17688).

Furthermore, a transgenic animal having a repertoire of human antibody genes is immunized with the gankyrin polypeptide, cells expressing the gankyrin polypeptide or lysates thereof to obtain the anti-gankyrin polypeptide antibody-producing cells, which are used to obtain human antibody against the gankyrin polypeptide using hybrodomas fused to myeloma cells (see International Patent Publication WO 92-03918, WO 93-2227, WO 94-02602, WO 94-25585, wO 96-33735 and WO 96-34096).

The monoclonal antibody-producing hybridomas thus constructed can be subcultured in the conventional culture liquid, or can be stored for a prolonged period of time in liquid nitrogen.

In order to obtain monoclonal antibodies from said hybridoma, there may be employed a method in which said hybridoma is cultured in the conventional method and the antibodies are obtained as the culture supernatant, or a method in which the hybridoma is administered to and grown in a mammal compatible with said hybridoma and the antibodies are obtained as the ascites. The former method is suitable for obtaining high-purity antibodies, whereas the latter is suitable for a large scale production of antibodies.

In addition to using a hybridoma to produce an antibody, immune cells that produce the desired antibody, for example the sensitized lymphocytes that have been immortalized with an oncogene, may be used to obtain the antibody.

A monoclonal antibody thus produced can also be obtained as a recombinant antibody by recombinant gene technology. For example, an anti-gankyrin polypeptide antibody gene may be cloned from the hybridoma or an immune cell such as a sensitized lymphocyte that produces antibodies, and is integrated into a suitable vector which is then introduced into a host to produce a recombinant antibody. Recombinant antibodies may also be used in the present invention (see, for example, Borrebaeck, C. A. K., and Larrick, J. W., THERAPEUTIC MONOCLONAL ANTIBODIES, published in the United Kingdom by MACMILLAN PUBLISHERS LTD. 1990).

Specifically, mRNA encoding the variable region (V region) of anti-gankyrin polypeptide antibody can be isolated from a hybridoma that produces the anti-gankyrin polypeptide antibody. The isolation of mRNA is conducted by preparing total RNA using a known method such as the guanidine ultracentrifugation method (Chirgwin, J. M. et al., Biochemistry (1979) 18, 5294-5299), the AGPC method (Chomzynski, P. and Sacci, N., Anal. Biochem. (1987) 162, 156-159), and then purifying mRNA from the total RNA using the mRNA Purification Kit (Pharmacia) and the like. Alternatively, mRNA can be prepared directly using the QuickPrep mRNA Purification kit (Pharmacia).

The mRNA obtained is used to synthesize the cDNA of the gene using a reverse transcriptase. The synthesis of cDNA can be effected using the AMV Reverse Transcriptase First-strand cDNA Synthesis Kit (Seikagaku Kogyo), and the like. Alternatively, for the synthesis and amplification of cDNA, the 5'-Ampli FINDER RACE kit (CLONTECH) and the 5'-RACE method (Frohman, M. A. et al., Proc. Natl. Acad. Sci. U.S.A. (1988) 85, 8998-9002; Belyavsky, A. et al., Nucleic Acids Res. (1989) 17, 2919-2932) that employs the polymerase chain reaction (PCR) may be used.

A DNA fragment of interest may be prepared from the PCR product thus obtained and ligated to a vector DNA. Furthermore, a recombinant vector is constructed from this, which is then introduced into *E. coli* for selection of colonies to prepare the desired recombinant vector. The base sequence of the desired DNA may be confirmed by a known method such as the dideoxy nucleotide chain termination method. Once the desired DNA encoding the V region of anti-gankyrin polypeptide antibody has been obtained, it may be ligated to DNA encoding the constant region (C region) of the desired antibody, which is then integrated into an expression vector. Alternatively, the DNA encoding the V region of the antibody may be integrated into an expression vector which already contains DNA encoding the C region of the antibody. The C region of antibody may be the one derived from the same animal species as the V region or the one derived from the different animal species from the V region.

In order to produce the anti-gankyrin polypeptide antibody for use in the present invention, the antibody gene is integrated as described below into an expression vector so as to be expressed under the control of the expression regulatory region, for example an enhancer and/or a promoter. Subsequently, the expression vector may be transformed into a host cell and the antibody can then be expressed therein.

For the expression of an antibody, DNA encoding the heavy chain (H chain) or the light chain (L chain) of the antibody may be separately integrated into an expression vector and the hosts are transformed simultaneously, or DNA encoding the H chain and the L chain may be integrated into a single expression vector and the host is transformed therewith (see International Patent Application WO 94-11523).

Antibodies for use in the present invention may be antibody fragments or modified versions thereof as long as they bind to gankyrin polypeptides. For example, as fragments of antibody, there may be mentioned Fab, F(ab')2, Fv or single-chain Fv (scFv) in which Fv's of the H chain and the L chain were ligated via a suitable linker. Specifically antibodies are treated with an enzyme, for example, papain or pepsin, to produce antibody fragments, or genes encoding these antibody fragments are constructed, and then introduced into an expression vector, which is expressed in a suitable host cell (see, for example, Co, M. S. et al., J. Immunol. (1994) 152, 2968-2976; Better, M. and Horwitz, A. H., Methods in Enzymology (1989) 178, 476-496; Plucktrun, A. and Skerra, A., Methods in Enzymology (1989) 178, 476-496; Lamoyi, E., Methods in Enzymology (1986) 121, 652-663; Rousseaux, J. et al., Methods in Enzymology (1986) 121, 663-669; Bird, R. E. et al., Trends Biotechnol. (1991) 9, 132-137).

scFv can be obtained by ligating the V region of the H chain and the V region of the L chain of an antibody. In the scFv, the V region of the H chain and the V region of the L chain are ligated via a linker, preferably a peptide linker (Huston, J. S. et al., Proc. Natl. Acad. Sci. U.S.A. (1988) 85, 5879-5883). The V region of the H chain and the V region of the L chain in the scFv may be derived from any of the above-mentioned antibodies. As the peptide linker for ligating the V regions, any single-chain peptide comprising, for example, 12-19 amino acid residues may be used.

DNA encoding scFv can be obtained using DNA encoding the H chain or the H chain V region of the above antibody and DNA encoding the L chain or the L chain V region of the above antibody as the template by amplifying the portion of the DNA encoding the desired amino acid sequence among the above sequences by the PCR technique together with the primer pair specifying the both ends thereof, and by further amplifying the combination of DNA encoding the peptide linker portion and the primer pair which defines that both ends of said DNA are ligated to the H chain and the L chain, respectively.

Once DNAs encoding scFv are constructed, an expression vector containing them and a host transformed with said expression vector can be obtained by the conventional methods, and scFv can be obtained using the resultant host by the conventional methods.

These antibody fragments may be antibody fragments part of which have undergone mutation, substitution, deletion, or insertion. These antibody fragments can also be produced by obtaining the gene thereof in a similar manner to that mentioned above and by allowing it to be expressed in a host. "Antibody" as used in the claim of the present application encompasses these antibody fragments.

As modified antibodies, anti-gankyrin polypeptide antibodies associated with various molecules such as polyethylene glycol (PEG) can be used. "Antibody" as used in the claim of the present application encompasses these modified antibodies. These modified antibodies can be obtained by chemically modifying the antibodies thus obtained. These methods have already been established in the art.

The anti-gankyrin polypeptide antibody of the present invention can be obtained as chimeric or humanized antibody using a known method.

The antibody gene constructed as above can be expressed by a known method to obtain the antibody. For example, promoters/enhancers for production of the gankyrin polypeptide described herein can be used.

For the production of anti-gankyrin polypeptide antibody for use in the present invention, any production system can be used, and the production system for the production of gankyrin polypeptide described herein can be used. For example, the production system for anti-gankyrin polypeptide antibody preparation comprises the in vitro or the in vivo production system. As the in vitro production system, there can be mentioned a production system which employs eukaryotic cells and the production system which employs prokaryotic cells. As the in vitro production system, there can be mentioned methods that use animals or that use plants. When animals are used, there are the production systems which employ mammals and insects.

As mammals, goats, pigs, sheep, mice, and cattle and, for example, transgenic animals thereof can be used (Glaser V., SPECTRUM Biotechnology Applications, 1993). Also as insects, silkworms can be used. Furthermore, when plants are used, tabacco, for example, such as *Nicotiana tabacum* can be used (Ma, J. K. et al., Eur. J. Immunol. (1994) 24, 131-138).

When an antibody is produced in in vitro or in vivo production systems, as described above, DNA encoding the H chain or the L chain of the antibody may be separately integrated into an expression vector and the hosts are transformed simultaneously, or DNA encoding the H chain and the L chain may be integrated into a single expression vector and the host is transformed therewith (see International Patent Application WO 94-11523).

Antibodies produced and expressed as described above can be separated from the inside or outside of the host cell and then may be purified to homogeneity. Separation and purification of the antibody for use in the present invention may be accomplished by, but not limited to, the separation and the purification methods conventionally used for protein purification.

For example, there can be mentioned chromatography columns such as affinity chromatography, filtration, ultrafiltration, salting-out, dialysis, SDS-polyacrylamide gel electrophoresis, isoelectric focusing and the like, from which methods can be selected and combined as appropriate for separation and purification of antibody (Antibodies: A Laboratory Manual, Ed Harlow and David Lane, Cold Spring Harbor Laboratory, 1988).

As columns for use in affinity chromatography, there can be mentioned Protein A column and Protein G column. Examples of the carriers used in the Protein A column are Hyper D, POROS, Sepharose F. F. (Pharmacia) and the like.

As chromatography other than the above-mentioned affinity chromatography, there can be mentioned, for example, ion exchange chromatography, hydrophobic chromatography, gel-filtration, reverse phase chromatography, adsorption chromatography, and the like (Strategies for Protein Purification and Characterization: A Laboratory Course Manual. Ed Daniel R. Marshak et al., Cold Spring Harbor Laboratory Press, 1986). These chromatographies can be carried out using a liquid chromatography such as HPLC, FPLC.

The concentration of antibody obtained as above can be determined by the measurement of absorbance or by the enzyme-linked immunosorbent assay (ELISA) and the like. Thus, when absorbance measurement is employed, the antibody obtained is appropriately diluted with PBS and then the absorbance is measured at 280 nm. In the case of human antibody, calculation is conducted using 1.40 OD at 1 mg/ml, though the absorption coefficient varies depending on the species and the subclass.

When the ELISA method is used, measurement is conducted as follows. Thus, 100 μl of goat anti-human IgG diluted to 1 μg/ml in 0.1 M bicarbonate buffer, pH 9.6, is added to a 96-well plate (manufactured by Nunc), and is incubated overnight at 4° C. to immobilize the antibody. After blocking, 100 μl each of appropriately diluted antibody of the present invention or a sample containing the antibody, or 100 μl of human IgG as the concentration standard is added, and incubated at room temperature for 1 hour.

After washing, 100 μl of 5000-fold diluted alkaline phosphatase-labeled anti-human IgG is added, and incubated at room temperature for 1 hour. After washing, the substrate solution is added and incubated, followed by the measurement of absorbance at 405 nm using the MICROPLATE READER Model 3550 (Bio-Rad) to calculate the concentration of the desired antibody.

Alternatively, BIAcore (Pharmacia) can be used for the measurement of antibody concentration.

The activity of anti-gankyrin polypeptide antibody of the present invention can be evaluated by a known method. For example, the activity of anti-gankyrin polypeptide antibody of the present invention can be evaluated by adding $^{125}$I-labeled anti-gankyrin polypeptide antibody to a plate on which gankyrin polypeptide has been immobilized, washing the plate according to a known method, and then measuring the radioactivity (Antibodies: A Laboratory Manual. Ed Harlow and David Lane, Cold Spring Harbor Laboratory, 1988).

As methods for determining the antigen-binding activity of anti-gankyrin polypeptide antibody for use in the present invention, there can be used ELISA, EIA (enzymeimmunoassay), RIA (radioimmunoassay), or the fluorescent antibody method.

When ELISA is employed, for example, a gankyrin polypeptide is added to a plate onto which anti-gankyrin polypeptide antibody has been immobilized, and then samples containing the desired anti-gankyrin polypeptide antibody, for example a culture supernatant of anti-gankyrin polypeptide antibody-producing cells or purified antibody, are added thereto. The second antibody that recognizes the anti-gankyrin polypeptide antibody labeled with an enzyme such as alkaline phosphatase is added, and the plate is incubated, washed. Then the enzyme substrate is added, and the absorbance is measured to evaluate the antigen-binding activity. As the gankyrin polypeptide, a fragment of the gankyrin polypeptide, a fragment comprising the C-terminal thereof, or a fragment comprising the N-terminal thereof may be used. For the evaluation of the activity of the anti-gankyrin polypeptide antibody of the present invention, BIAcore (Pharmacia) can be used.

By using such methods, a method of detecting or determining a gankyrin polypeptide may be conducted, said method comprising contacting said antibody to a sample expected to contain said gankyrin polypeptide and detecting or determining an immune complex between said antibody and said gankyrin polypeptide.

Specifically, when ELISA is employed, for example, a sample containing a gankyrin polypeptide is added to a plate onto which anti-gankyrin polypeptide antibody has been immobilized, and then anti-gankyrin polypeptide antibody is added thereto.

The second antibody that recognizes the anti-gankyrin polypeptide antibody labeled with an enzyme such as alkaline phosphatase is added, and the plate is incubated and washed. Then, after adding the enzyme substrate such as p-nitrophenyl phosphate thereto and determining absorbance, the presence of the gankyrin polypeptide in the sample can be evaluated. As the gankyrin polypeptide, a fragment of the gankyrin polypeptide, a fragment comprising the C-terminal thereof, or a fragment comprising the N-terminal thereof may be used. For the evaluation of the activity of the anti-gankyrin polypeptide antibody of the present invention, BIAcore (Pharmacia) can be used.

The method of detecting or determining the gankyrin polypeptide of the present invention is important in various experiments that employ gankyrin polypeptides since it can specifically detect or determine gankyrin polypeptides.

The present invention includes a nucleotide (DNA or RNA) capable of selectively hybridizing the gene of the present invention or a nucleotide derivative such as an antisense oligonucleotide or ribozyme and the like. The present invention also includes an antisense oligonucleotide that hybridizes any of the sites in the nucleotide sequence as set forth in SEQ ID NO: 1. The antisense oligonucleotide is preferably an antisense oligonucleotide to at least 20 or more contiguous nucleotides in the base sequence as set forth in SEQ ID NO: 1. More preferably, it is an antisense oligonucleotide in which said at least 20 or more contiguous nucleotides in the nucleotide sequence as set forth in SEQ ID NO: 1 contain a translation initiation codon. For example, the antisense oligonucleotide of the present invention contains SEQ ID NO: 8. Furthermore, for example, the antisense oligonucleotide of the present invention is one that contains SEQ ID NO: 9.

As used herein "antisense oligonucleotide" may contain one or a plurality of nucleotide mismatches as long as nucleotides corresponding to nucleotides constituting a given region of DNA or mRNA are all complementary and DNA or mRNA and the oligonucleotide can selectively and stably hybridize to the base sequence as set forth in SEQ ID NO: 1. "Selectively and stably hybridize" as used herein means that they have a homology of at least 70%, preferably 80%, more preferably 90%, more preferably 95% or more of the base sequence on at least 20, preferably 30 contiguous nucleotide sequence regions.

According to one embodiment of the present invention, the antisense oligonucleotide has the nucleotide sequence as set forth in SEQ ID NO: 8. Furthermore, according to one embodiment of the present invention, the antisense oligonucleotide has the nucleotide sequence as set forth in SEQ ID NO: 9.

When the oligonucleotide derivative for use in the present invention is a deoxyribonucleotide, each structure is as shown in formula (I):

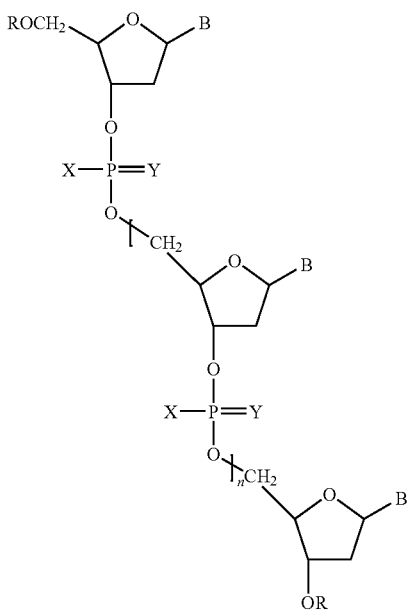

wherein X may be independently any of oxygen (O), sulfur (S), a lower alkyl group, or a primary amine or a secondary amine; Y may be independently any of oxygen (O) or sulfur (S); B is selected from the group consisting of adenine, guanine, thymine, and cytosine, and is mainly a complementary oligonucleotide to the DNA or the mRNA of the human gankyrin gene; R is independently hydrogen (H) or a dimethoxytrityl group or a lower alkyl group; and n is 7 to 28.

Preferred oligonucleotide derivatives may be not only unmodified oligonucleotides, but, as described hereinbelow, modified oligonucleotides. Examples of such modifications include, for example, lower alkyl phosphonate-modifications such as the above-mentioned methylphosphonate type or the ethylphosphonate type, and the phosphorothioate modifications or the phosphoroamidate modifications.

Examples of

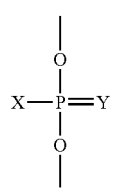

are represented by the following formula (II):

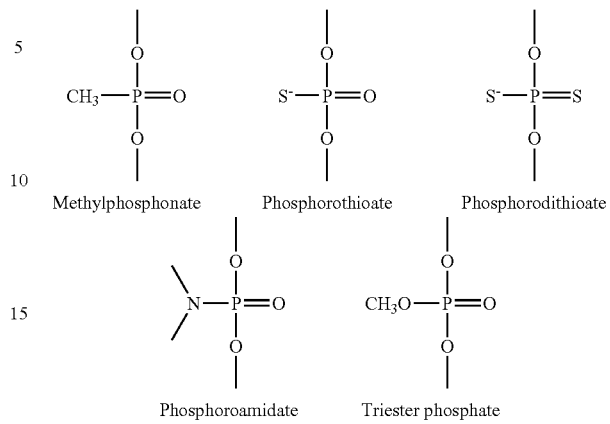

These antisense oligonucleotide derivatives can be obtained by a conventional method as shown below. An oligonucleotide of Formula (1) in which X and Y are O may be readily synthesized using a commercially available DNA synthesizer (for example the one manufactured by Applied Biosystems). Synthesis can be effected by the solid phase synthesis using hydrogen phosphonate (T. Atkinson, & M. Smith, in Oligonucleotide Synthesis: A Practical Approach, ed. M. J. Gait, IRL Press, 35-81 (1984); M. H. Caruthers, Science 230, 281 (1985); A. Kume, et al., J. Org. Chem., 49, 2139 (1984); B. C. Froehler, et al., Tetrahedron Lett. 27, 469 (1986); P. J. Garegg, et al., ibid, 27, 4051 (1986); B. S. Sproat, et al., in Oligonucleotide Synthesis: A Practical Approach, ed. M. J. Gait, IRL Press, 83-115 (1984); S. L. Beaucage & M. H. Caruthers, Tetrahedron Lett., 22, 1859-1862 (1981); M. D. Matteucci and M. H. Caruthers, Tetrahedron Lett., 21, 719-722 (1980); M. D. Matteucci & M. H. Caruthers, J. Am. Chem. Soc., 103, 3185-3191 (1981)

A triester phosphate modification in which X is a lower alkoxy group can be obtained by, for example, a conventional method in which an oligonucleotide that has been obtained by chemical synthesis is treated with a solution of tosyl chloride in DMF/methanol/2,6-lutidiene (Moody H. M. et al., Nucleic Acids Res., 17, 4769-4782 (1989)).

An alkyl phosphonate modification in which X is an alkyl group can be obtained by, for example, using phosphoamidite (M. A. Dorman, et al., Tetrahedron Lett. 40, 95-102 (1984); K. L. Agarwal & F. Riftina, Nucleic Acids Res., 6, 3009-3024 (1979)).

A triester phosphorothioate modification in which X is S can be obtained by a solid phase synthesis using sulfur (C. A. Stein, et al., Nucleic Acids Res., 16, 3209-3221 (1988)), or a solid phase synthesis using tetraethyltiraum disulfide (H. Vu and B. L. Hirschbein, Tetrahedron Lett. 32, 3005-3008 (1991).

A phosphorodithioate modification in which both X and Y are S can be obtained by, for example, a solid phase synthesis in which a bisamidite is converted to a thioamidite, on which is acted sulfur to yield said modification (W. K.-D. Brill, et al., J. Am. Chem. Soc., 111, 2321-2322 (1989)).

A phosphoroamidate modification in which X is a primary amine or a secondary amine can be obtained by, for example, a solid phase synthesis in which hydrogen phosphonate is treated with a primary or secondary amine (B. Froehler, et al., Nucleic Acids Res., 16, 4831-4839 (1988)). Alternatively the amidite may be oxidized with tert-butyl hydroperoxide to yield said modification (H. Ozaki, et al., Tetrahedron Lett., 30, 5899-5902 (1989)).

Purification and the confirmation of purity can be carried out by high performance liquid chromatography and polyacrylamide gel electrophoresis. The confirmation of molecular weight can be carried out by Electrospray Ionization Mass Spectrometry or Fast Atom Bombardment-Mass Spectrometry. The antisense oligonucleotide of the present invention may be obtained by any synthetic method or from any source as long as it has a sequence that hybridizes to the base sequence of DNA or mRNA encoding a human gankyrin polypeptide.

The antisense oligonucleotide derivative of the present invention acts on the human gankyrin polypeptide-producing cells, as shown hereinbelow in Example 7, to bind to DNA or mRNA encoding the human gankyrin polypeptide and thereby to inhibit its transcription or translation and promote the decomposition of mRNA, resulting in the suppression of human gankyrin polypeptide expression. Eventually it exhibits an effect of suppressing the actions of human gankyrin polypeptide. The actions of human gankyrin polypeptide suppressed by the antisense oligonucleotide derivative of the present invention includes, for example, the suppression of the colony-forming ability in soft agar by the cells described in Example 7.

The antisense oligonucleotide derivative of the present invention can be mixed with an appropriate base to formulate an external preparation such as a liniment, a cataplasm and the like.

It can also be mixed, as desired, with an excipient, an isotonic agent, a solubilizer, a stabilizer, an antiseptic, a soothing agent or the like to formulate a tablet, powder, granules, a capsule, a liposome capsule, an injection, a solution, a nasal drop, and the like as well as a lyophilized preparation. They can be prepared according to a conventional method.

The antisense oligonucleotide derivative of the present invention may be applied to the patient by either directly administering to the affected area of the patient or administering into the blood vessel thereby allowing the substance to be delivered to the affected area. Furthermore, an antisense encapsulating material that enhances prolonged action and membrane permeability may be used. There may be mentioned, for example, liposome, poly-L-lysine, lipid, cholesterol, Lipofectin® (a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in membrane filtered water, from Invitrogen Corp.) or derivatives thereof.

Preferably the dosage of the antisense oligonucleotide derivative of the present invention can be adjusted as appropriate depending on the condition of the patient to employ a preferred amount. For example, preferred dosage is in the range of 0.1 to 100 mg/kg, preferably 0.1 to 50 mg/kg.

The antisense oligonucleotide of the present invention is useful in inhibiting the expression of gankyrin polypeptide and thereby in suppressing the biological activity of gankyrin polypeptide. An inhibitor of the expression of gankyrin polypeptide containing the antisense oligonucleotide of the present invention can suppress the biological activity, i.e. carcinogenicity, of gankyrin, and therefore, is useful as a therapeutic agent for cancer or hypertrophic disorders.

EXAMPLES

The present invention is now explained in more detail with reference to the following examples.

Example 1 cDNA Cloning by the Subtraction Method

Using the subtraction method (Nakayama, H. et al., Develop. Growth Differ. (1996) 38, 141-151), cDNAs of the genes that are specifically expressed in hepatic cancer were cloned.

From surgical specimens of a 55-year old male patient, tissues of stage 3 hepatic cancer as defined in the code of handling primary hepatic cancer (compiled by the Japan Hepatic Cancer Study Group) and the normal liver tissue were removed. From each tissue, total RNA was extracted using the TRIsol reagent (manufactured by GIBCO BRL). From the total RNA, double stranded cDNA was synthesized with oligo-dT primers using the cDNA synthesis kit (manufactured by Pharmacia). After digesting the cDNA with a restriction enzyme RsaI, a linker adapter (Nakayama, H. et al., Develop. Growth Differ. (1996) 38, 141-151) was added thereto, and these cDNAs were amplified by the PCR method using pimers (Nakayama, H. et al., Develop. Growth Differ. (1996) 38, 141-151). When the cDNA from the normal liver tissue was amplified by the PCR method, primers that were end-labeled with biotin were used.

An excessive amount of double stranded cDNA derived from the normal liver tissue was mixed with a small amount of double stranded cDNA derived from hepatic cancer, and the mixture was then heat-denatured to make it single-stranded, followed by annealing to double strands. Most of the cDNAs derived from hepatic cancer tissue that were also expressed in the normal liver tissue hybridize with cDNAs derived from the normal liver tissue and come to have biotin labels. However, molecules that are specific for the hepatic cancer tissue form double strands there between and thereby do not come to have biotin labels. Accordingly, double stranded cDNAs having biotin labels were eliminated and cDNA molecules specific for the hepatic cancer tissue were concentrated.

cDNA molecules that are specific for the hepatic cancer tissue were amplified by the PCR method and were concentrated by repeating the same procedure by 5 times. This gave 250 bp of cDNA fragments specific for the hepatic cancer tissue derived from the human hepatic cancer tissue. In order to isolate the full-length cDNA, a cDNA library was constructed from a human placenta, the mouse NIH/3T3 cell line, and a rat placenta by a conventional method and were ligated to the λZAPII phage vector (manufactured by Strategene). Using the above 250 bp human cDNA fragments as a probe, the above placenta cDNA libraries were screened under a highly stringent condition.

Thus, they were hybridized in a hybridization solution (5×SSPE, 50% formamide, 5×Denhardt's solution, 0.5% SDS, 100 µg/ml denatured DNA, 10% dextran sulfate) at 42° C., followed by washing under a condition of 1×SSC, 1.0% SDS, 65° C. (Sambrook, J. et al., Molecular Cloning, Cold Spring Harbor Laboratory Press (1989)). As a result, 1542 bp of human cDNA containing 678 bp Of ORF was obtained.

The 678 bp of ORF in this cDNA was PCR-amplified, which was then used as a probe in a screening of cDNA libraries of the rat placenta and mouse NIH/3T3 cell lines under a less stringent condition. Thus, they were hybridized in a hybridization solution (5×SSPE, 50% formamide, 5×Denhardt's solution, 0.5% SDS, 100¯.tg/ml denatured DNA, 10% dextran sulfate) at 37° C., follow¯d by washing under a condition of 1×SSC, 1.0% SDS, 37° C. (Sambrook, J. et al., Molecular Cloning, Cold Spring Harbor Laboratory Press (1989)).

As a result, cDNAs derived from the rat and the mouse were isolated. The nucleotide sequence of these cDNAs were determined using a conventional method, and the nucleotide sequence in turn was used to determine amino acid sequence. The estimated amino acid sequences of human, rat, and mouse cDNAs are shown by a one-letter code and are compared, as shown in the following Table 1. The polypeptides having these amino acid sequences were designated as gankyrin. The human gankyrin gene and the mouse gankyrin gene had a 90% homology on the base sequence level and a 93% homology on the amino acid sequence level. On the other hand, human gankyrin gene and the rat gankyrin gene had a 91% homology on the base sequence level and a 94% homology on the amino acid sequence level.

In this table, the upper 3 lines represent ankyrin sequences, and the bottom 6 lines represent ankyrin repeats in the amino acid sequence of the gankyrin polypeptide of the present invention.

Figure 15:
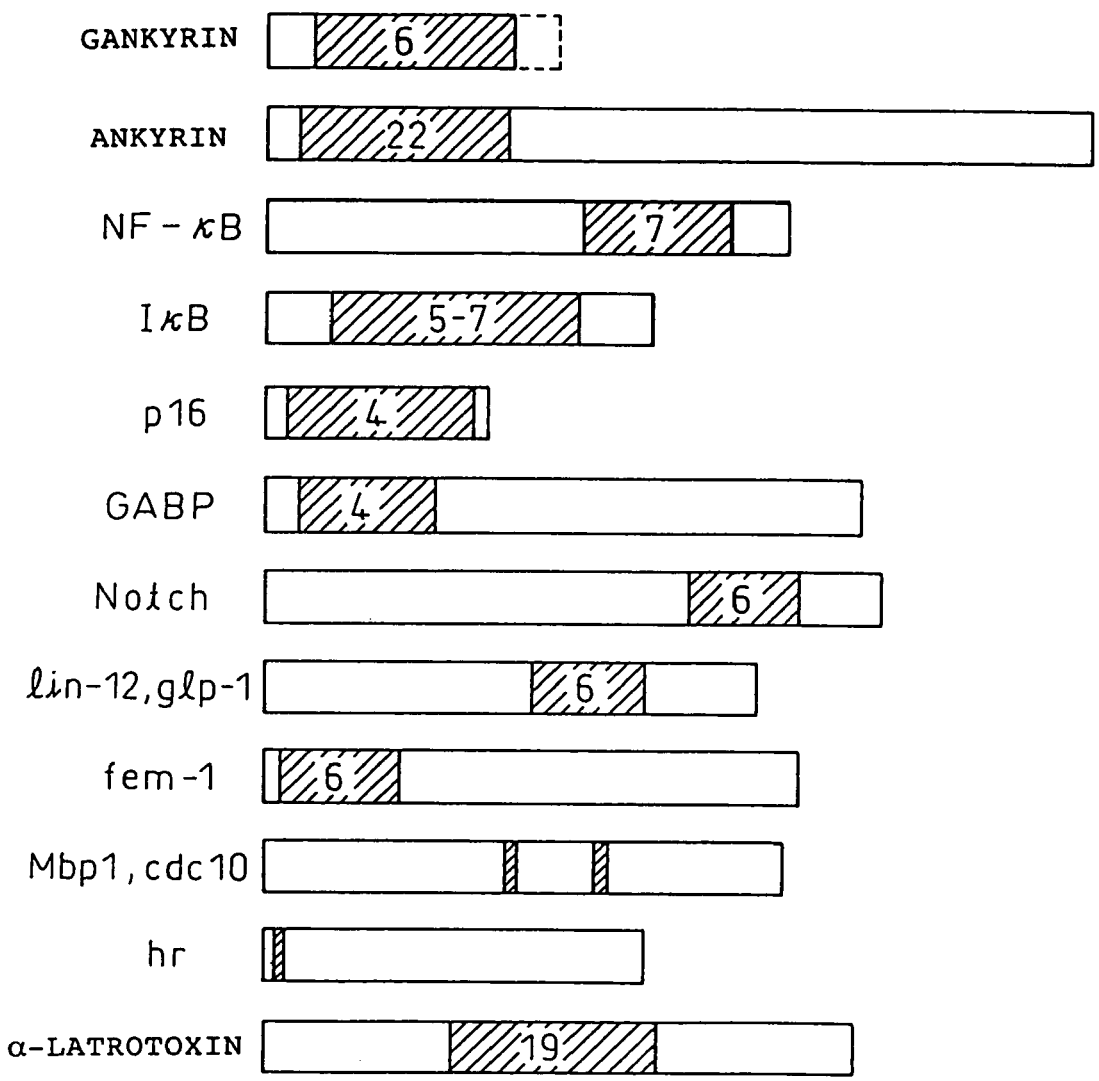
FIG. 15 is a drawing that shows the position and the number of repetition of ankyrin repeats in various proteins.

Furthermore, FIG. 15 shows the site and the number of ankyrin repeats in various proteins.

In order to determine the position of the gankyrin gene on the chromosome, fluorescence in situ hybridization was conducted. Thus, lymphocytes isolated from human blood were cultured in an minimum essential medium (MEM) supplemented with 10% fetal bovine serum and phytohemagglutinin (PHA) at 37° C. for 68 to 72 hours. This lymphocyte culture was treated with 0.18 mg/ml BrdU (manufactured by

TABLE 1

```
Human   MEGCVSNLMVCNLAYSGKLEELKESILADKSLATRTDQDSRTALHWACSAGHTEIVEFLL
Mouse   MEGCVSNIMICNLAYSGKLDELKERILADKSLATRTDQDSRTALHWACSAGHTEIVEFLL
Rat     MEGCVSNLMVCNLAYNGKLDELKESILADKSLATRTDQDSRTALHWACSAGHTEIVEFLL Human   QLGVPVNDKDDAGWSPLHIAASAGRDEIVKALLGKGAQVNAVNQNGCTPLHYAASKNRHE
Mouse   QLGVPVNDKDDAGWSPLHIAASAGRDEIVKALLVKGAHVNSVNQNGCTPLHYAASKNRHE
Rat     QLGVPVNEKDDAGWSPLHIAASAGRDEIVKALLIKGAQVNAVNQNGCTALHYAASKNRHE Human   IAVMLLEGGANPDAKDHYEATAMHRAAAKGNLKMIHILLYYKASTNIQDTEGNTPLHLAC
Mouse   ISVMLLEGGANPDAKDHYDATAMHRAAAKGNLKMVHILLFYKASTNIQDTEGNTPLHLAC
Rat     IAVMLLEGGANPDAKNHYDATAMHRAAAKGNLKMVHILLFYKASYNIQDTEGNTPLHLAC Human   DEERVEEAKLLVSQGASIYIENKEEKTPLQVAKGGLGLILKRMVEG       (SEQ ID NO: 2)
Mouse   DEERVEEAKFLVTQGASIYIENKEEKTPLQVAKGGLGLILKRLAESEEASM  (SEQ ID NO: 3)
Rat     DEERVEEAKLLVTQGASIYIENKEEKTPLQVAKGGLGLILKRIVESEEASM  (SEQ ID NO: 5)
```

The nucleotide sequence of human gankyrin is shown in SEQ ID NO: 1 and the amino acid sequence thereof is shown in SEQ ID NO: 2. The nucleotide sequence of mouse gankyrin is shown in SEQ ID NO: 3 and the amino acid sequence thereof is shown in SEQ ID NO: 4. The nucleotide sequence of rat gankyrin is shown in SEQ ID NO: 5 and the amino acid sequence thereof is shown in SEQ ID NO: 6. In addition, it was estimated that in the amino acid sequences of gankyrins, the region from amino acid Met at position 1 to amino acid Leu at position 13 is a signal sequence.

The amino acid sequence of the human gankyrin polypeptide thus obtained had 5.5 ankyrin repeats (Lambert, S. et al., Proc. Natl. Acad. Sci. U.S.A. (1990) 87, 1730-1734). This is shown in the following Table 2.

TABLE 2

```
ANK consensus    G TPLHLAAR GHVEVVKLLLD GADVNA TK
SEQ ID NO: 10      A I SQ NNLDIAEV  K    NPD D
                   V K   T M R     Q    SI  N
                                   E 1st repeat       DSRTALHWACSAGHTEIVEFLLQLGVPVNDKDD
SEQ ID NO: 11

2nd repeat       AGWSPLHIAASAGRDEIVKALLGKGAQVNAVNQ
SEQ ID NO: 12

3rd repeat       NGCTPLHYAASKNRHEIAVMLLEGGANPDAKDH
SEQ ID NO: 13

4th repeat       YEATAMHRAAAKGNLKMIHILLYYKASTNIQDT
SEQ ID NO: 14

5th repeat       EGNTPLHLACDEERVEEAKLLVSQGASIYIENK
SEQ ID NO: 15

6th repeat       EEKTPLQVAKGGLGLILKRMVEG
SEQ ID NO: 16
```

Sigma) to synchronize the cell cycle of the cell population. The cells of which the cell cycle were synchronized were washed three times with a serum-free medium. After the cell cycle arrest was removed, they were cultured again in a MEM containing 2.6 µg/ml thymidine (manufactured by Sigma) at 37° C. for 6 hours. Cells were collected, subjected to a standard procedure comprising a hypotonic treatment, fixation, and air drying to prepare slides of chromosome specimens.

Phage DNA (Sambrook, J. et al. Molecular Cloning, supra) having an about 8.0 kb gankyrin gene insert was biotin-labeled by nick translation with dATP and biotin-16-dCTP at 15° C. for one hour using the BRL BioNick label kit according to the instructions (Herg et al., Proc. Natl. Acad. Sci. U.S.A. 89:9509-9513 (1992)).

Using this as a probe, fluorescence in situ hybridization (FISH) was carried out (Herg et al., Proc. Natl. Acad. Sci. U.S.A. 89:9509-9531 (1992); Herg et al., Chromosoma, 102; 325-332 (1993)).

Thus, a slide was first treated at 55° C. for one hour to attach the chromosome on the glass slides. After an RNase treatment, the slide was denatured with 70% formamide in 2×SSC at 70° C. for 2 minutes, and then dehydrated with ethanol. The probe was denatured in a hybridization mixture containing 50% formamide, 10% dextran sulfate and human cotI DNA at 75° C. for 5 minutes. After incubation at 37° C. for 15 minutes to suppress the repeat sequence, the probe was added to the above denatured slide. After overnight hybridization, the slide was washed with 50% formamide in 2×SSC at 37° C., and then in 1×SSC at 60° C.

After biotin was detected with fluorescence-labeled FITC-bound avidin (manufactured by Vector Laboratories), the slide was stained with DAPI (manufactured by Sigma), a fluorescent reagent for staining DNA, to generate a G/Q-band pattern on the chromosome. Use of this method enables the generation of graded band patterns peculiar to the chromosome with a fluorescent reagent for staining DNA, and chromosome assigning and chromosome mapping (location).

Using a cooled charge-coupled device (CCD) camera (manufactured by Photometrics) that is a TV camera capable of detecting a very weak light, 21 metaphase (mitotic period) images were photographed. By over lapping the FISH signal and the DAPI band-forming chromosome, the FISH map data was assigned to the chromosome band (Hery et al., Methods in Molecular Biology: In situ hybridization protocols (K. H. A Choo. ed), p. 35-49 (1994), Human Press, Clifton, N.J.).

Under the condition used, hybridization efficiency for this probe was about 81%. Thus, out of 100 mitotic figures tested, 80 figures have shown signals on a pair of chromosomes. Since DAPI band formation was used in order to identify specific chromosomes, signals from the probe were assigned to the long arm of the X chromosome. Furthermore, detailed positions was determined by putting together 10 photographs. The result is shown in FIG. 1. Since no other loci were detected by the FISH under the condition used, the probe T4-11 was assigned to the chromosome X region q21.3-q22.2.

Figure 2:
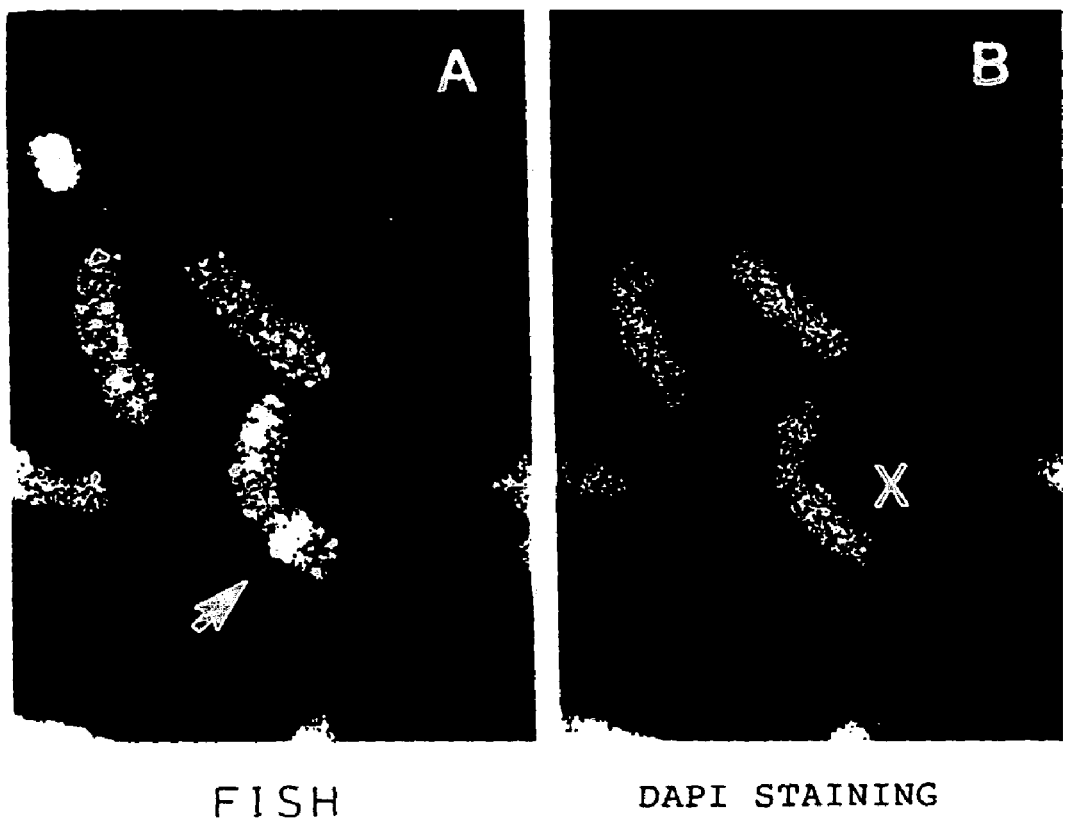
FIG. 2 is a photograph showing that a gankyrin gene on the chromosome in human lymphocytes was fluorescence-stained by the in situ hybridization method and detected.

The result (fluorescence staining) of the in situ hybridization obtained is shown in FIG. 2.

Example 2

A Study on the Expression Level of a Gankyrin Gene in the Tissue

In order to study the expression of a gankyrin gene, various tissues and cells were homogenized in the TRIzol reagent (manufactured by GIBCO BRL). Total RNA (20 μg) was denatured, and was separated by electrophoresis in a 1.0% agarose gel containing 2.2 M formaldehyde.

The gel was blotted to the Hybond N+ nylon membrane (manufactured by Amersham), and was hybridized to [α-$^{32}$P] dCTP-labeled cDNA fragment (250 bp of human gankyrin cDNA) in a rapid hybridization buffer (Rapi-hyb buffer, manufactured by Amersham). After hybridization, the filter was washed under a stringent condition comprising the wash buffer containing 0.1×SSC and 0.1% SDS at 65° C. for 30 minutes, and then was exposed to a film at −80° C. The filter was cut into strips, which were hybridized again to a probe for 18S rRNA as an internal standard. The expression level of RNA was evaluated by quantifying the autoradiogram by a scanning densitometer (manufactured by Ato).

Figure 3:
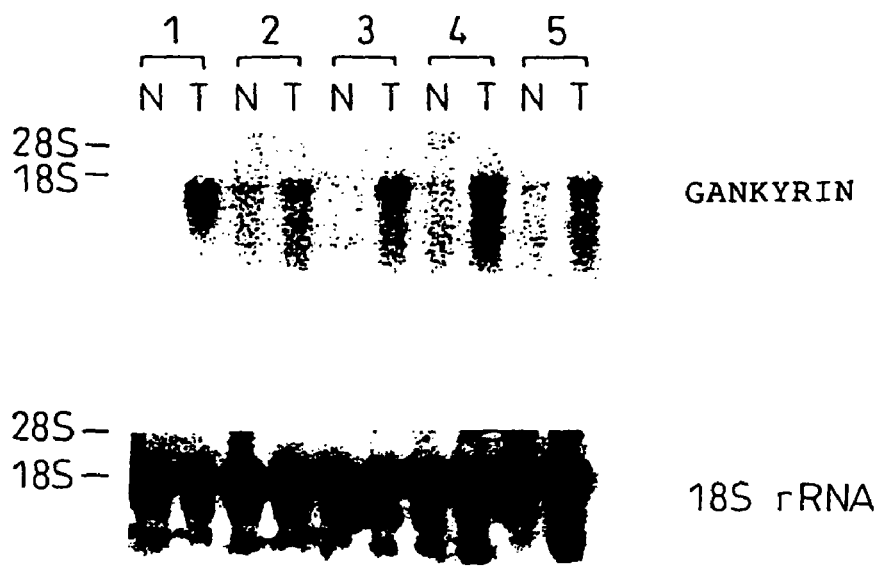
FIG. 3 is an electrophoregram showing the result that mRNAs from the normal liver tissue (N) and the hepatic cancer tissue (T) of 5 patients with hepatic cancer (1 to 5) were detected by the Northern method using human gankyrin cDNA as a probe.

The result of samples from the hepatic cancer tissue (T) and the hepatic non-cancer tissue (N) is shown in FIG. 3. The lower part represents the result of the internal standard and the upper part represents the result detected with the cDNA probe of human gankyrin. It was shown that gankyrin mRNA is expressed in excessive amounts in the hepatic cancer tissue alone.

The result (positive tests/total tests) for the human cancer tissues other than the liver is shown below.

| | |
|---|---|
| RCC (kidney cell carcinoma) | 0/20 |
| Testicular carcinoma | 0/5 |
| Ovary carcinoma | 0/5 |
| Gastric cancer | 4/4 |

As a result, gankyrin mRNA was expressed in excessive amounts in the tissue of gastric cancer among the cancer tissues tested.

Figure 4:
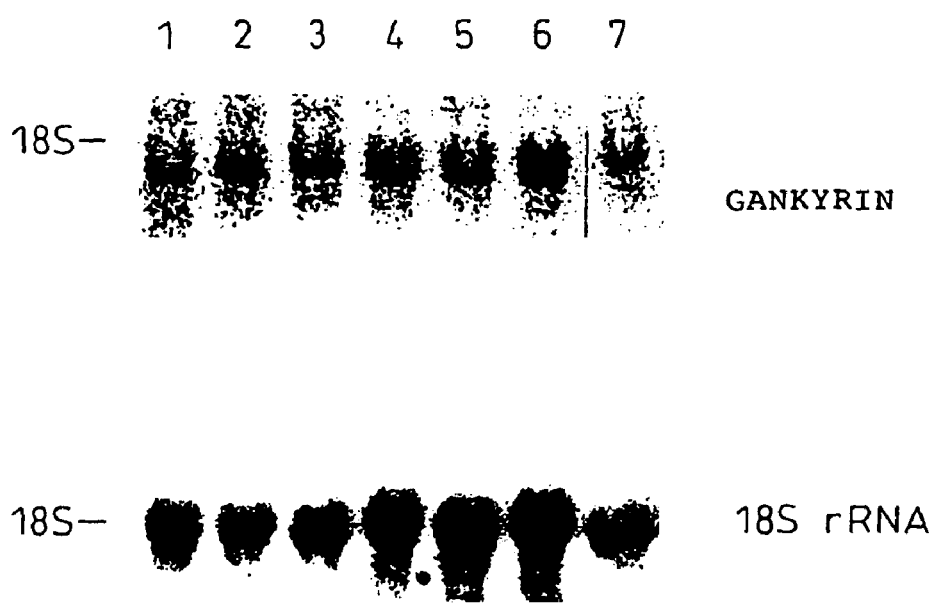
FIG. 4 is an electrophoregram showing the result that mRNAs from various human cell lines were detected by the Northern method using human gankyrin cDNA as a probe.

The results for various cell lines, i.e. human cell line HepG2 (lane 1), Hela (lane 2), K562 (lane 3), NC65 (lane 4), NEC8 (lane 5), T24 (lane 6), and IMR90 (lane 7) are shown in FIG. 4. The expression of gankyrin mRNA was observed in some cell lines.

Figure 5:
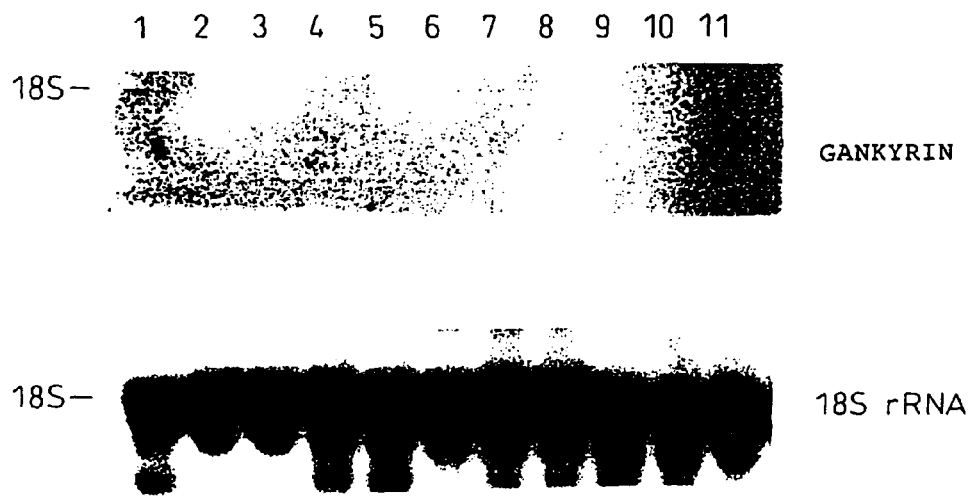
FIG. 5 is an electrophoregram showing the result that mRNAs from various normal tissues were detected by the Northern method using human gankyrin cDNA as a probe.

The result for various normal tissues, i.e. liver (lane 1), spleen cells (lane 2), pancreas (lane 3), heart (lane 4), adrenal (lane 5), thyroid (lane 6), placenta (lane 7), ovary (lane 8), testis (lane 9), kidney (lane 10), and lung (lane 11) are shown in FIG. 5. As shown in FIG. 5, there was little expression of gankyrin mRNA in normal human tissues.

The above result confirmed the specific and high expression of gankyrin mRNA in the cancer tissue.

Example 3

Preparation of Antibody to Gankyrin Polypeptide and Immunohistochemical Analysis Thereof For preparation of anti-gankyrin polypeptide antibody, a peptide Met-Glu-Gly-Cys-Val-Ser-Asn-Leu-Met-Val-Cys-Asn-Leu-Ala-Tyr (SEQ ID NO: 7) corresponding to the C-terminal region of gankyrin was immunized. The peptide was linked to keyhole limpet hemocyanin, and then was immunized to a rabbit. On day 14, 42, and 56 after the immunization, the rabbit was immunized again to obtain antiserum.

The antiserum obtained was affinity purified with the above immobilized peptide to obtain polyclonal antibody (Fmoc Chemistry, Research Gevetic Inc.). The reactivity and/or specificity to the gankyrin polypeptide of the present invention were confirmed by the Western blot analysis. Thus, an expression plasmid for a gankyrin gene was added to a TNT expression system (manufactured by Promega) to obtain a translation product (gankyrin polypeptide). At this time, [$^{35}$S]-methionine was added to the system to synthesize [$^{35}$S]-methionine-labeled human gankyrin polypeptide. Non-labeled gankyrin polypeptide was also synthesized using the same condition.

[$^{35}$S]-methionine-labeled and non-labeled human gankyrin polypeptides were subjected to polyacrylamide gel electrophoresis (the condition is described below), and the migration pattern of the non-labeled substance was analyzed by the Western blot method. Thus, the migration gel of the non-labeled substance was transferred to an Immobilon transfer membrane (manufactured by Millipore), and was blocked in a Tris buffer containing 5% bovine serum albumin (BSA). Then the above blotting membrane was incubated with the polyclonal antibody diluted 1:2000 to 1:10000 in a Tris buffer, 0.1% Tween 20, and BSA at 4° C. for 16 hours.

The blotting membrane was repeatedly washed in the Tris buffer and 0.1% Tween 20 and then was incubated with anti-rabbit immunoglobulin antibody labeled with horseradish peroxidase as the 2nd antibody at room temperature for 1 hour. After washing, it was allowed to develop color with an electrochemiluminescence reagent (manufactured by Amersham).

On the other hand, for the migration gel for the labeled substance, the migration pattern of gankyrin polypeptide was confirmed by autoradiography. As a result, a Western blot band of the non-labeled substance was observed corresponding to the autoradiography band of the labeled substance, indicating that the polyclonal antibody recognizes the gankyrin gene product.

Figure 8:
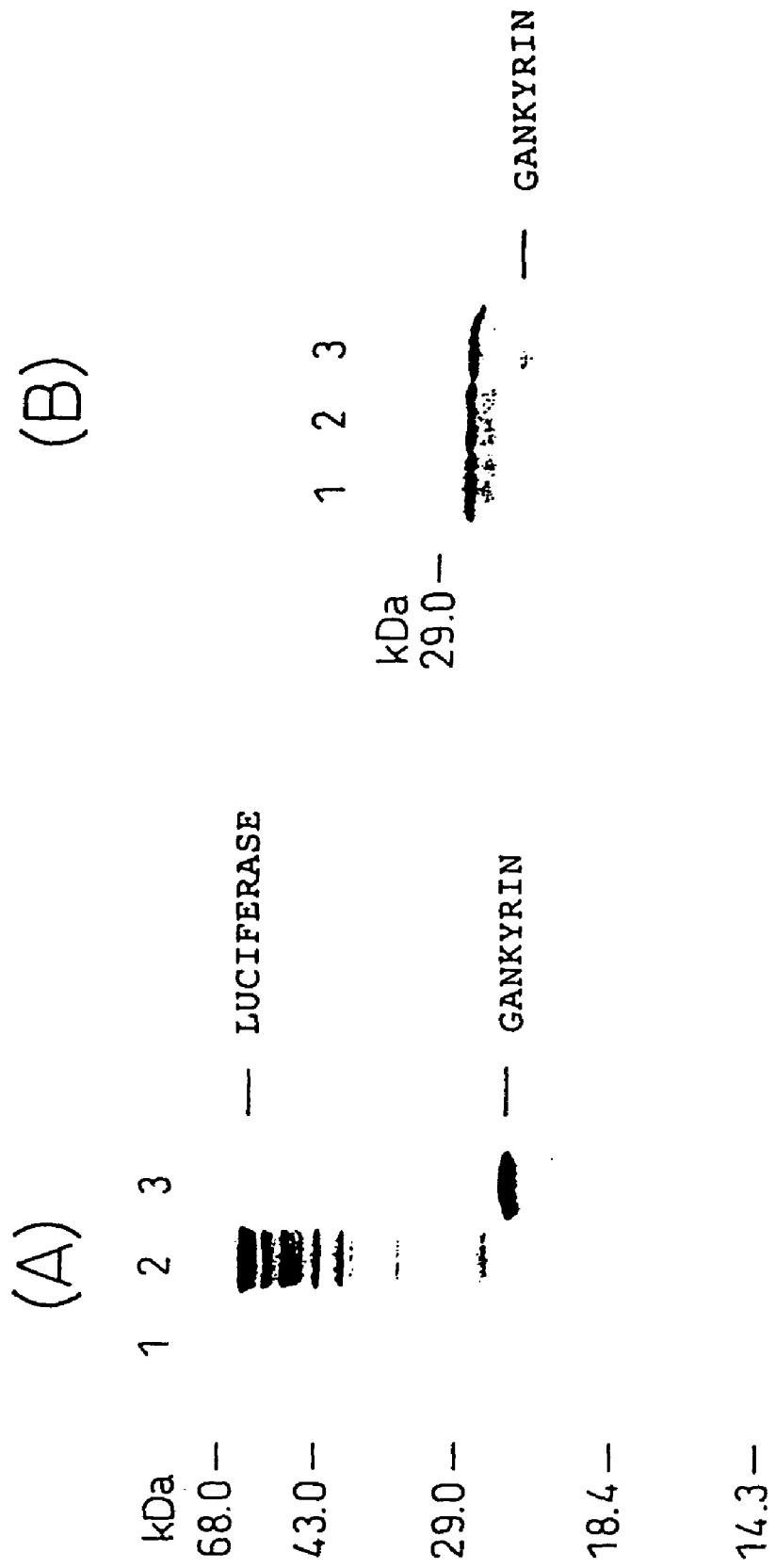
FIG. 8A is an electrophoregram showing the result that the in vitro translated gankyrin gene products were detected in a similar manner to FIG. 6.
FIG. 8B is an electrophoregram showing the result that the in vitro translated gankyrin gene products (non-labeled) were detected in a similar manner to FIG. 6.

In a Western blot analysis conducted simultaneously using a TNT expression system containing no template DNA and a luciferase cDNA expression product, the present polyclonal antibody, no such specific bands were observed, confirming the specificity of the polyclonal antibody to gankyrin polypeptide. FIG. 8A shows a result on products of an in vitro-translated labeled gankyrin gene. The template (−) (lane 1), positive control (luciferase cDNA corresponding to about 60 kDa) (lane 2), and gankyrin (lane 3). The result of Western blot analysis using anti-gankyrin polypeptide antibody on the in vitro-translated gankyrin gene products (non-labeled) is shown in FIG. 8B. Each lane represents the template (−) (lane 1), positive control (luciferase cDNA corresponding to about 60 kDa) (lane 2), and gankyrin (lane 3).

Figure 6:
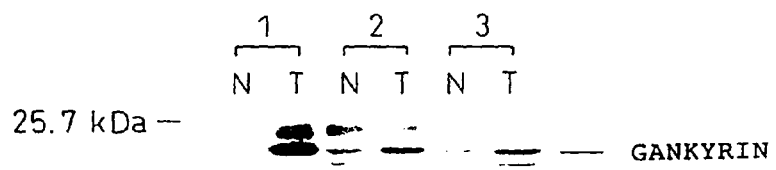
FIG. 6 is an electrophoregram showing the result that gankyrin polypeptides in cell lysates from the normal tissue (N) and the hepatic cancer tissue (T) of 3 patients with hepatic cancer (1 to 3) were detected by the Western blot method using anti-gankyrin polypeptide antibody.

FIG. 6 shows a result of an experiment in which gankyrin polypeptides in the lysates of the hepatic non-cancer tissue (N) and the hepatic cancer tissue (T) of three patients with hepatic cancer were detected by a Western blot method using anti-gankyrin polypeptide antibody that was affinity-purified as described above. Similarly the level of mRNA shown in Example 2, more gankyrin polypeptides were detected in the hepatic cancer tissue than in the hepatic non-cancer tissue.

Figure 7:
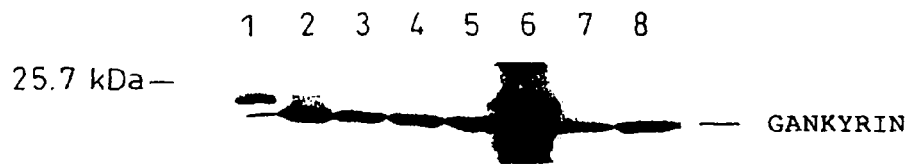
FIG. 7 is an electrophoregram showing the result that gankyrin polypeptides in cell lysates from various human cell lines were detected by the Western blot method using anti-gankyrin polypeptide antibody.

FIG. 7 shows the result of an experiment in which gankyrin polypeptides from the total cell lysates of human cell lines, i.e. HepG2 (ATCC catalogue 1994 (American Type Culture Collection)) (lane 1), HeLa (ATCC catalogue 1994 (American Type Culture Collection)) (lane 2), T24 (ATCC catalogue 1994 (American Type Culture Collection)) (lane 3), NC65 (Hoehn, W. and Schroeder, F. H., Invest. Urol. (1978) 16, 106) (lane 4), NEC8 (Human Science Research Resource bank, Cell/gene catalogue, 2nd edition, 1995) (lane 5), Jurkat (ATCC catalogue 1994 (American Type Culture Collection)) (lane 6), 293 (ATCC catalogue 1994 (American Type Culture Collection)) (lane 7) and COS-7 (ATCC catalogue 1994 (American Type Culture Collection)) (lane 8) were detected by a Western blot method using the anti-gankyrin polypeptide antibody that was affinity-purified as described above. As a result, the expression of gankyrin polypeptide was confirmed in all cell lines.

Total cell extracts and tissue extracts were prepared from $3\sim5\times10^6$ cells lysated in a modified buffer for radioisotope-labeled immunoprecipitation comprising 50 mM Tris-HCl, pH 7.4, 400 mM NaCl, 1% SDS, 1% Triton X-100, 1% deoxycholic acid, and 5 mM EDTA, and then subjected to ultrasonic treatment to shear DNA. Immediately before use, a phosphatase inhibitor comprising 15 mM β-glycerophosphate, 2 mM sodium pyrophosphate and 1 mM $Na_3VO_4$, and a protease inhibitor comprising aprotinin, leupeptin and phenylmethyl sulfonyl fluoride were added to all extracts.

Samples were separated on a SDS-polyacrylamide gel electrophoresis (PAGE), and the gel used in the SDS-PAGE was transferred to an Immobilon transfer membrane (manufactured by Millipore), followed by blocking in a Tris buffer containing 5% bovine serum albumin (BSA). Then the above blotting membrane was incubated together with the above primary antiserum or antibody diluted to 1:2000 to 1:10000 in the Tris buffer, 0.1% Tween 20, and BSA at 4° C. for 16 hours. The blotting membrane was repeatedly washed in a Tris buffer and 0.1% Tween 20. Then it was incubated with anti-rabbit immunoglobulin antibody or anti-mouse immunoglobulin antibody labeled with horseradish peroxidase as the 2nd antibody at room temperature for 1 hour. After washing, it was allowed to develop color with an electrochemiluminescence reagent (manufactured by Amersham).

Example 4

Characterization of Gankyrin Polypeptide

A 678 bp cDNA encoding human gankyrin polypeptide (Example 1) was ligated to PMKIT-NEO mammal expression vector (Shinsaibo Kogaku Jikken Protocol (New Cell Engineering Experiment Protocol) P. 259, The University of Tokyo, the Institute of Medical Science, ed., Shujunsha) in a sense and antisense direction. The SRa promoter in this vector can direct the constitutive synthesis of RNA from the inserted DNA. The PMKIT-NEO vector has a neomycin resistant gene suitable for selection of transformants.

Thirty micrograms of the plasmid construct was transfected into NIH 3T3 cells (Jainchill, J. F. et al., J. Virol. (1969) 4, 549-553) by the calcium phosphate method. Forty eight hours after the transfection, G418 was added to the culture medium to a concentration of 1000 μg/ml. Individual colonies were isolated and were propagated for further analysis. Thus, 5 sense clones, 5 antisense clines, and 5 control clones were established, and these clones were characterized by in vitro growth, morphology, cell cycle, and tumorigenicity The doubling time was determined from the growth curve. The cells were cultured in a 2-layer soft agar comprising a bottom layer (DMEM, 10% FCS, 0.6% agar) and an upper layer (DMEM, 10% FCS, 0.3% agar). A 35 mm soft agar plate was inoculated with $5\times10^3$ cells, incubated at 37° C. for 4 to 5 weeks, and then the cells were counted. The mean colony count of the clonies comprising 15 or more cells was 25±2 for the control clone, and 123±1 for the sense clone. Accordingly, the enhancement in the ability of colony formation by the cells that express gankyrin polypeptide in soft agar was demonstrated.

Tumorigenicity in the NIH 3T3 cell line was tested by transferring subcutaneously $1\times10^6$ cells to 4-week old female nude mice (Flanagan, S. P. Genet. Res. (1966) 8, 295-309). Each of 5 clonal cell lines comprising a mock construct and a clonal cell line containing a sense human gankyrin construct was subcutaneously transplanted to 3 mice (a total of 18 mice) at $1\times10^6$ cells/mouse. Tumor formation was observed for 3 months after subcutaneous transplantation. Measurement of tumor was conducted using a linear caliper in two right angles by the same observer. For cell cycle analysis, flow cytometry was used.

As a result, tumor formation when the control vector-containing cells were inoculated was 0 clone (no tumor formation) out of 4 clones whereas tumor formation when the sense vector-containing cell clones were inoculated was 3 clones out of 4 clones. It is evident, therefore, that the transplantation of gankyrin polypeptide-expressing cells to mice shows tumorigenicity. In one clone in which no tumor was formed, the expression level of gankyrin mRNA was lower than other 3 clones.

In a cultured human kidney cell line 293, apoptosis is induced by removing serum from the culture medium and dead cells increase. Using this cell line, the effect of gankyrin gene on the induction of apoptosis was investigated. Prior to the experiment, each gene was transfected into the 293 cells by the calcium phosphate coprecipitation method using 10 μg of the above pMKIT-NEO vector, and a plurality of clones in which each gene was stably introduced were obtained, which were used for the subsequent experiment.

It was shown, at this time, that the mean value of the colony focus number obtained from the G418 selection medium in three transfection experiments was 56±4 for the control clone, 70±4 for the sense clone, and 23±3 for the antisense clone. It was demonstrated, therefore, that gankyrin polypeptide is involved in the promotion of cell growth and suppression of apoptosis induction.

Using each 293 cell clone, $2\times10^5$ cells were plated to a 60 mm tissue culture plate (Nunc GmbH). After the removal of serum, cells were trypsinized and the numbers of the suspended cells and the attached cells, and the number of dead cells were counted by trypan blue staining to determine the ratio of the number of the dead cells to the number of total cells.

To analyze the number of apoptosis cells, a histochemical method was employed. Thus, cells of each clone were grown on a cover slip for 48 hours until they reach a density of 60% saturation. After the removal of serum, apoptosis cells were stained by the ApopTa apoptosis detection kit (manufactured by Oncor), and examined under a light microscope to count the ratio of the number of the apoptosis cells to that of total cells.

In the above two experiments, the ratio (%) of the number of total cells stained with trypan blue to the number of the total cells and the ratio (%) of the apoptosis cells to the number of total cells were 33±5% and 45±5% for the control clone, and 59±6% and 30±2% for the sense clone, respectively. It was demonstrated, therefore, that apoptosis and cell death by gankyrin gene products are suppressed.

For each clone, $2 \times 10^5$ cells were plated to a 10 mm tissue culture plate. After incubation, serum was removed to induce apoptosis. In order to analyze the fragmentation of gene DNA between nucleosomes, which is characteristic to the apoptosis cells, the above cells were scraped at predetermined times and the supernatants were collected together with the attached cells. The cells were resuspended in 0.25 ml of TBE (45 mM Tris-borate, 1 mM EDTA, pH 8.0) containing 0.25% NP-40 and 0.1 mg/ml of RNase.

After incubating at 37° C. for 30 minutes, the extracts were further treated with 1 mg/ml of proteinase K at 37° C. for 30 minutes. Then, 30 µl of the extract was subjected to a 1.7% agarose gel electrophoresis in the presence of 0.5 µg/ml of ethidium bromide. As a result, the ladder-like electrophoretic pattern due to DNA fragmentation between nucleosomes was decreased in the sense gankyrin gene-introduced cells as compared to the control cells. It was demonstrated from these three experiments, therefore, that gankyrin gene products acts on apoptosis induction in a suppressive manner. This is a characteristics observed for many other tumorigenic genes, thereby indicating that the gankyrin gene is a tumorigenic gene.

Example 5

Interaction of Gankyrin Polypeptides

The human gankyrin cDNA obtained in Example 1 was ligated to a pCMV4-3HA' vector (Brockman, J. A. et al., Molecular and Cellular Biology (1995) 15, 2809-2818) that has the cytomegalovirus enhancer/promoter and having the nucleotide sequence of influenza virus hemagglutinin (HA) epitope to construct a plasmid pCMV4-3HA+gankyrin that expresses a fusion polypeptide comprising gankyrin and influenza virus HA.

Furthermore, a human gankyrin coding sequence was inserted to a vector pGEX (manufactured by Pharmacia) to construct a plasmid that expresses a fusion polypeptide comprising glutathione S-transferase (GST) and gankyrin.

Using 10 µg of pCMV4-3HA+gankyrin, the 293 cells were transiently transfected by the calcium phosphate method. pGEX-gankyrin was introduced into $E.\ coli$, and the production of GST-gankyrin fusion polypeptide was induced with 1 mM IPTG. After collecting the cells by centrifuging at 4° C., the cells were dissolved by sonication in PBS containing Triton X100. The cell lysate was mixed with the total cell extract from the 293 cell transformant, which was incubated at 4° C. for 16 hours.

The GST-fused polypeptide was collected on glutathione-Sepharose 4B (manufactured by Pharmacia) and was analyzed by the Western blot method using anti-Rb antibody, anti-NFκB p50 antibody, and anti-NFκB p65 (all manufactured by Santa Crutz).

The preparation of cell extracts and immunoprecipitates was conducted as follows. To an IP buffer containing 50 mM HEPES (pH 7.5), 150 mM NaCl, 2.5 mM EGTA, 1 mM DTT, 0.1% Tween 20, 10% glycerol, a protease inhibitor, and a phosphatase inhibitor, the cells were suspended, sonicated, and then centrifuged at 10000×g, 4° C., for 10 minutes. Using Protein A-Sepharose CL4b (manufactured by Pharmacia) precoated with anti-HA antibody, anti-Rb antibody, anti-NFκB p50 antibody or anti-NFκB p65 antibody, the supernatant was precipitated at 4° C. for 16 hours.

Proteins that precipitated on the beads were washed ten times in the IP buffer. The precipitate in the 2×SDS sample buffer was separated by SDS-polyacrylamide gel electrophoresis, and was analyzed by Western blot method with anti-HA antibody, anti-Rb antibody, anti-NFκB p50 antibody or anti-NFκB p65 antibody.

The result is shown below.

Figure 9:
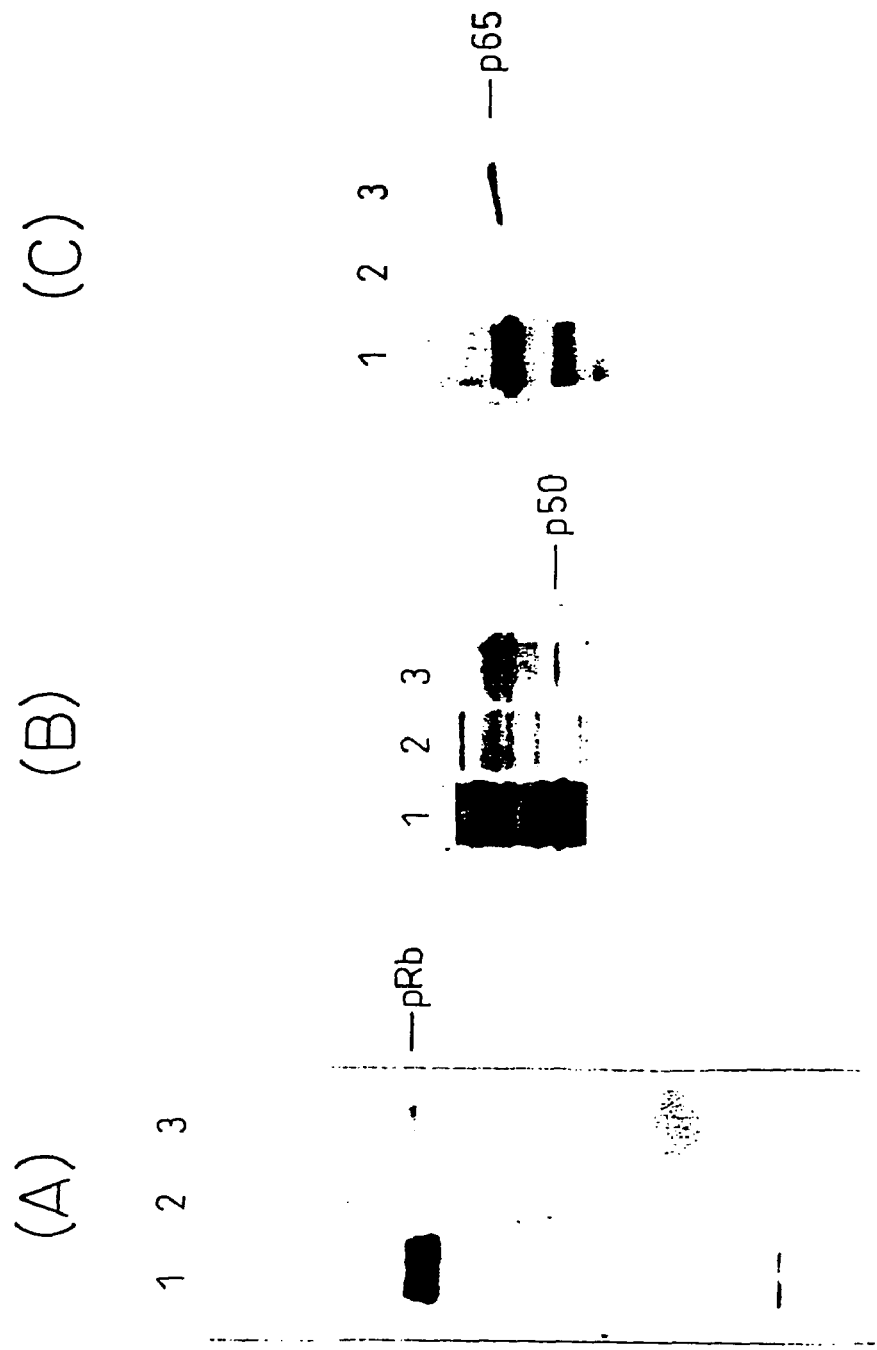
FIG. 9 is an electrophoregram showing the result that fusion polypeptides comprising gankyrin polypeptide and GST were expressed in *Escherichia coli* (*E. coli*) and then were detected using various antibodies.

FIG. 9 shows the result in which cell lysates were used in vitro. GST alone or a fusion polypeptide of GST and gankyrin was expressed in $E.\ coli$, which was then harvested. The GST alone or the GST-gankyrin fusion polypeptide was mixed with human 293 cells, and then precipitated with glutathione-bound Sepharose, which was electrophoresed.

The result is shown that was obtained after the electrophoresed gel was transferred to a nitrocellulose membrane and was detected with (A) anti-Rb antibody, (B) anti-p50 antibody, and (C) anti-p65 antibody. In (A), lanes indicate, from left to right, the results of a human 293 cell lysate alone, a precipitate obtained by mixing a human 293 cell lysate with the above $E.\ coli$-expressed GST polypeptide and then by precipitating it with glutathione-bound Sepharose, and a precipitate obtained by mixing a human 293 cell lysate with an $E.\ coli$-expressed fusion polypeptide and then by precipitating it with glutathione-bound Sepharose.

In (B), lanes indicate, from left to right, the results of a human 293 cell lysate alone, a precipitate obtained by mixing a human 293 cell lysate with an $E.\ coli$-expressed GST polypeptide and then by precipitating it with glutathione-bound Sepharose, and a precipitate obtained by mixing a human 293 cell lysate with an $E.\ coli$-expressed fusion polypeptide and then by precipitating it with glutathione-bound Sepharose. In (C), lanes indicate, from left to right, the results of a human 293 cell lysate alone, a precipitate obtained by mixing a human 293 cell lysate with an $E.\ coli$-expressed GST polypeptide and then by precipitating it with glutathione-bound Sepharose, and a precipitate obtained by mixing a human 293 cell lysate with an $E.\ coli$-expressed fusion polypeptide and then by precipitating it with glutathione-bound Sepharose.

The results of in vivo experiments on the cells are shown in FIG. 10. By immunoprecipitating the lysate of human 293 cells that express gankyrin fused to HA with (A) anti-Rb antibody, (B) anti-p50 antibody, or (C) anti-p65 antibody, and then by detecting with anti-HA antibody, an HA-fused gankyrin polypeptide was detected. In (A), lanes indicate the results of a human 293 cell lysate that was transformed with a vector containing no gankyrin gene and precipitated with a non-specific immunoglobulin (lane 1) or anti-Rb antibody (lane 2), which was then electrophoresed and detected with anti-HA antibody, and a human 293 cell lysate that was transformed with a vector containing a gankyrin gene and precipitated with a non-specific immunoglobulin (lane 3) or anti-Rb antibody (lane 4), which was then electrophoresed and detected with anti-HA antibody.

In (B), lanes indicate the results of a human 293 cell lysate that was transformed with a vector containing no gankyrin gene and precipitated with a non-specific immunoglobulin (lane 1) or anti-p50 antibody (lane 2), which was then electrophoresed and detected with anti-HA antibody, a human 293 cell lysate that was transformed with a vector containing a gankyrin gene and precipitated with a non-specific immunoglobulin (lane 3) or anti-p50 antibody (lane 4), which was then electrophoresed and detected with anti-HA antibody, and a human 293 cell lysate that was transformed with a vector containing a gankyrin gene and then electrophoresed (lane 5) and detected with anti-HA antibody.

In (C), lanes indicate the results of a human 293 cell lysate that was transformed with a vector containing no gankyrin gene and precipitated with a non-specific immunoglobulin (lane 1) or anti-p65 antibody (lane 2), which was then electrophoresed and detected with anti-HA antibody, a human 293 cell lysate that was transformed with a vector containing a gankyrin gene and precipitated with a non-specific immunoglobulin (lane 3) or anti-p65 antibody (lane 4), which was then electrophoresed and detected with anti-HA antibody, and a human 293 cell lysate that was transformed with a vector containing a gankyrin gene and then electrophoresed (lane 5) and detected with anti-HA antibody.

The results of in vivo experiments on the cells are shown in FIG. 11. By immunoprecipitating the lysate of human 293 cells that express a fusion polypeptide comprising HA and gankyrin, and then detecting with (A) anti-Rb antibody, or (B) anti-p50 antibody, Rb and p65 were detected, respectively.

In (A), lanes indicate the results of a human 293 cell lysate that was transformed with a vector containing no gankyrin gene, electrophoresed, and detected with anti-Rb antibody (lane 1), a human 293 cell lysate that was transformed with a vector containing no gankyrin gene and precipitated with a non-specific immunoglobulin (lane 2) or anti-HA antibody (lane 3), which was then electrophoresed and detected with anti-Rb antibody, a human 293 cell lysate that was transformed with a vector containing a gankyrin gene and precipitated with a non-specific immunoglobulin (lane 3) or anti-HA antibody (lane 4), which was then electrophoresed and detected with anti-Rb antibody.

In (B), lanes indicate the results of a human 293 cell lysate that was transformed with a vector containing no gankyrin gene and precipitated with a non-specific immunoglobulin (lane 1) or anti-HA antibody (lane 2), which was then electrophoresed and detected with anti-p65 antibody, a human 293 cell lysate that was transformed with a vector containing a gankyrin gene and precipitated with a non-specific immunoglobulin (lane 3) or anti-HA antibody (lane 4), which was then electrophoresed and detected with anti-p65 antibody, and a human 293 cell lysate that was transformed with a vector containing a gankyrin gene and then electrophoresed (lane 5) and detected with anti-p65 antibody.

These results indicated that the gankyrin polypeptide interacts with Fb or NFκB in the cells (in vivo).

Example 6

Cell Cycle and Gankyrin Gene Expression

The cell cycle of NIH/3T3 cells was fixed at the early G1 period by serum starvation for 72 hours, and serum was added again to synchronize cell cycle. Cells were lyzed, mRNA was extracted, and detected using gankyrin cDNA as a probe. Thus, after mRNA was amplified by the PCR method with cDNA of the coding region of mouse gankyrin as a template, mRNA was detected by the Northern blot method using $^{32}$P-random primed labeled product as a probe.

Flow cytometry was used for the analysis of cell cycle by various cell means. Thus, cells were washed in PBS containing no $Ca^{2+}$ or $Mg^{2+}$, and were subjected to trypsin treatment. Then after the cells were washed with DMEM containing 10% FCS and collected, the cells were washed again in the sample buffer and resuspended, and then were fixed in 70% ethanol. The cells were stained with PI (Propiodium iodine), and determined by a flow cytometer.

Figure 12:
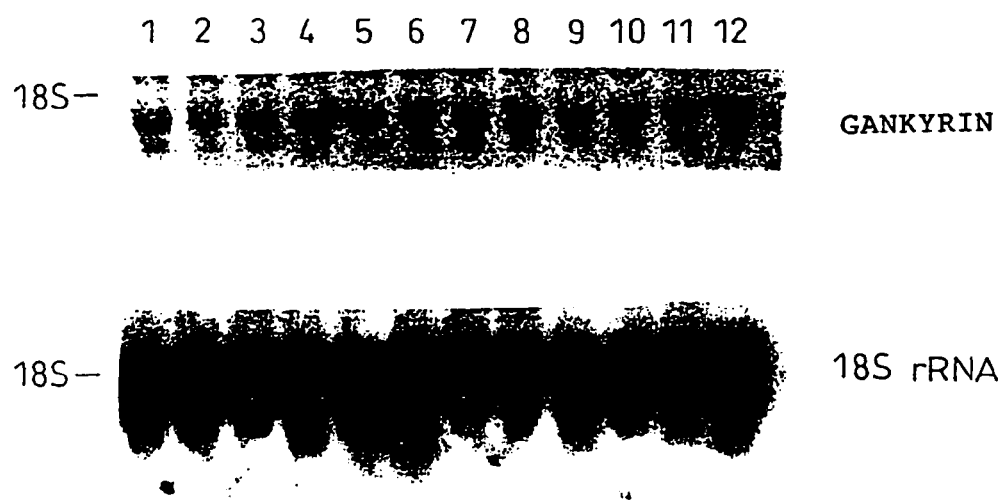
FIG. 12 is an electrophoregram showing the result that mRNAs in various cell cycles of the NIH/3T3 cells were detected by the Northern method using mouse gankyrin cDNA as a probe.

FIG. 12 shows the results. In FIG. 12, each lane represents the result at 1 hour (lane 1), 3 hours (lane 2), 6 hours (lane 3), 9 hours (lane 4), 12 hours (lane 5), 15 hours (lane 6), 18 hours (lane 7), 21 hours (lane 8), 24 hours (lane 9), 27 hours (lane 10), 30 hours (lane 11), and 33 hours (lane 12) after the re-addition of serum. One to 9 hours (lane 1 to 4) corresponds to the G1 period, 12 to 18 hours (lane 5 to 7) corresponds to the S period, 21 to 24 hours (lane 8 to 9) corresponds to the G2+M period, and 27 hours or after (lane 10) returns to the G1 period, again.

The result of the detection of mRNA expression in the cells grown at various concentrations is shown in FIG. 13. In this figure, the results of cell concentration $1 \times 10^6$ cells/100 mm dish (lane 1), $2 \times 10^6$ cells (lane 2), $3 \times 10^6$ cells (lane 3), and $4 \times 10^6$ cells (lane 4) are shown.

The result of detection of mRNA that is expressed during the process of liver regeneration after partial hepatic resection in mice is shown in FIG. 14. The results before partial hepatic resection (lane 1), and 1 hour (lane 2), 6 hours (lane 3), 24 hours (lane 4), 48 hours (lane 5), 72 hours (lane 6), and 168 hours (lane 7) after partial hepatic resection are shown.

When gankyrin mRNA was examined by the NIH3T3 cells for which cell cycle was synchronized, gankyrin expression was found to vary depending on the cell cycle. In the partially removed liver also, expression was found to vary depending on the cell cycle. These facts indicated that the expression of gankyrin, associated with the progress of cell cycle, increases from the G1 phase to the S phase, suggesting its association with cell cycle regulation.

Example 7

Inhibitory Effects of an Antisense Strand on Hepatic Cancer Cells

Using a human hepatic cancer cell line HepG2, human gankyrin antisense oligonucleotide derivative (sequence: ACCCCTCCATTTCGCTGTCC) (SEQ ID NO: 8) and (TTAGACACACACCCCTCCAT) (SEQ ID NO: 9) were studied for their effect of suppressing the growth of hepatic cells. As the culture medium, RPMI1640 (Nissui) supplemented with 2% fetal calf serum (FCS) was used.

A 35 mm culture plate containing 1 ml culture liquid was incubated overnight at 37° C. in a $CO_2$ incubator, to which were added $1 \times 10^2$ HepG2 cells that were made single cells by a 0.25% trypsin treatment and pipetting. After 24 hours, it was replaced with 1 ml of the culture liquied containing human gankyrin antisense oligonucleotide (0, 2.5, and 10 μg/ml) that contains the initiation codon of a gankyrin gene, and was further cultured for 4 days. A mass of 30 cells or more was defined as a colony, and the number of colonies was counted under an inverted microscope. Thus, the number of colonies when a sense oligonucleotide was added was 95±7%, whereas the number of colonies when an antisense oligonucleotide was added decreased to 70±5%, relative to 100% of the control to which distilled water was added.

Human gankyrin antisense oligonucleotide had a suppressive effect on the formation of colonies. As a result, it was revealed that an antisense oligonucleotide containing the initiation codon of gankyrin gene suppresses the growth of the hepatic cancer cell line HepG2 cells.

INDUSTRIAL APPLICABILITY

Since the gankyrin polypeptide of the present invention shows the elevation of colony-forming ability of cells, the suppression of tumorigenicity, and apoptosis induction in mice, it was shown to have carcinogenecity. The gankyrin polypeptide and DNA encoding it are useful for elucidation of the mechanism of action of oncogenesis. A screening method using a gankyrin polypeptide, antibody to a gankyrin polypeptide, a method of detecting or determininng a gankyrin polypeptide using it, and an antisense oligonucleotide to DNA encoding a gankyrin polypeptide are also useful for elucidation of the mechanism of action of oncogenesis.

Reference to the microorganisms deposited under the Patent Cooperation Treaty, Rule 13-2, and the name of the Depository organ Depository Organ Name: the National Institute of Bioscience and Human Technology, Agency of Industrial Science and Technology Address: 1-3, Higashi 1-chome, Tsukuba-shi, Ibaraki, Japan Organism (1)

Name: *Escherichia coli* DH5α [pBS-t4-11]

Accession number: FERM BP-6128

Date deposited: Sep. 29, 1997

The invention claimed is:

1. A method for inhibiting the growth of hepatic cancer cells, wherein said hepatic cancer cells express (a) a polypeptide having the sequence of amino acid 14 (Ala) to amino acid 226 (Gly) of SEQ ID NO: 2, or (b) a polypeptide encoded by the DNA sequence of SEQ ID NO: 1; the method comprising administering an antisense oligonucleotide capable of specifically and stably hybridizing to at least 20 contiguous nucleotides in the nucleotide sequence as shown in SEQ ID NO: 1, wherein the antisense oligonucleotide is represented by the following formula:

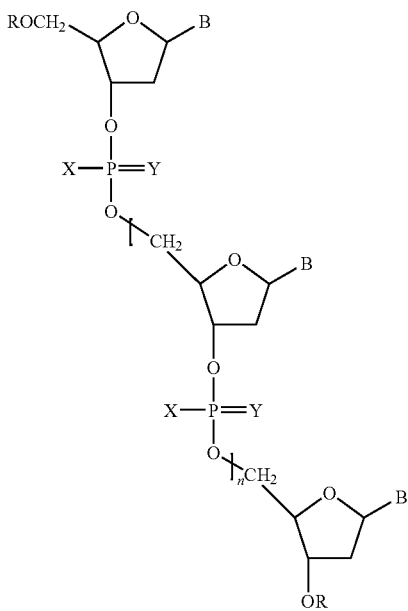

wherein X is independently any of oxygen (O), sulfur (S), a lower alkyl group, a primary amine or a secondary amine; Y is independently any of oxygen (O) or sulfur (S); B is selected from the group consisting of adenine, guanine, thymine and cytosine; R is independently hydrogen (H), a dimethoxytrityl group or a lower alkyl group; and n is 18 to 28, wherein the antisense oligonucleotide comprises the nucleotide sequence as set forth as SEQ ID NO: 8.

2. A method for inhibiting the growth of hepatic cancer cells, wherein said hepatic cancer cells express (a) a polypeptide having the sequence of amino acid 14 (Ala) to amino acid 226 (Gly) of SEQ ID NO: 2, or (b) a polypeptide encoded by the DNA sequence of SEQ ID NO: 1; the method comprising administering an antisense oligonucleotide capable of specifically and stably hybridizing to at least 20 contiguous nucleotides in the nucleotide sequence as shown in SEQ ID NO: 1, wherein the antisense oligonucleotide is represented by the following formula:

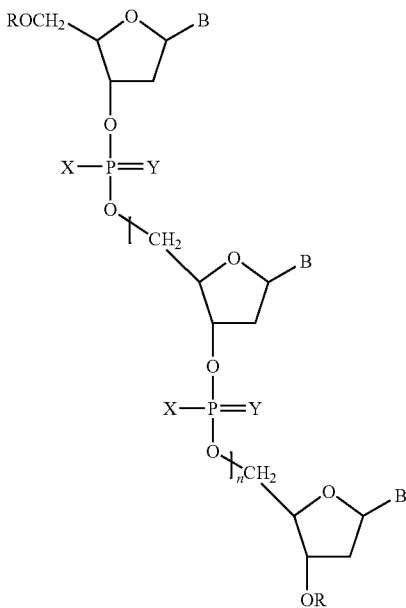

wherein X is independently any of oxygen (O), sulfur (S), a lower alkyl group, a primary amine or a secondary amine; Y is independently any of oxygen (O) or sulfur (S); B is selected from the group consisting of adenine, guanine, thymine and cytosine; R is independently hydrogen (H), a dimethoxytrityl group or a lower alkyl group; and n is 18 to 28, wherein the antisense oligonucleotide comprises the nucleotide sequence as set forth as SEQ ID NO: 9.

3. The method of claim 1, wherein the antisense oligonucleotide is administered with an antisense encapsulating material.

4. The method of claim 2, wherein the antisense oligonucleotide is administered with an antisense encapsulating material.

5. The method of claim 3, wherein the antisense encapsulating material is a liposome, poly-L-lysine, lipid, cholesterol or a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE).

6. The method of claim 4, wherein the antisense encapsulating material is a liposome, poly-L-lysine, lipid, cholesterol a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE).

* * * * *

SEQUENCE LISTING

```
<160> NUMBER OF SEQ ID NOS: 16

<210> SEQ ID NO 1
<211> LENGTH: 780
<212> TYPE: DNA
<213> ORGANISM: Homo sapiens
<220> FEATURE:
<221> NAME/KEY: CDS
<222> LOCATION: (97)..(774)

<400> SEQUENCE: 1
tggtgaagct ctaacggctg ttttgactgg cgtagccgga gccggcgacg tgaggcgggc         60
gttgctcgcg cgacaagtag ttgctgggac agcgaa atg gag ggg tgt gtg tct        114
                                         Met Glu Gly Cys Val Ser
                                           1               5 aac cta atg gtc tgc aac ctg gcc tac agc ggg aag ctg gaa gag ttg        162
Asn Leu Met Val Cys Asn Leu Ala Tyr Ser Gly Lys Leu Glu Glu Leu
             10                  15                  20 aag gag agt att ctg gcc gat aaa tcc ctg gct act aga act gac cag        210
Lys Glu Ser Ile Leu Ala Asp Lys Ser Leu Ala Thr Arg Thr Asp Gln
         25                  30                  35 gac agc aga act gca ttg cac tgg gca tgc tca gct gga cat aca gaa        258
Asp Ser Arg Thr Ala Leu His Trp Ala Cys Ser Ala Gly His Thr Glu
     40                  45                  50 att gtt gaa ttt ttg ttg caa ctt gga gtg cca gtg aat gat aaa gac        306
Ile Val Glu Phe Leu Leu Gln Leu Gly Val Pro Val Asn Asp Lys Asp
 55                  60                  65                  70 gat gca ggt tgg tct cct ctt cat att gcg gct tct gct ggc cgg gat        354
Asp Ala Gly Trp Ser Pro Leu His Ile Ala Ala Ser Ala Gly Arg Asp
                 75                  80                  85 gag att gta aaa gcc ctt ctg gga aaa ggt gct caa gtg aat gct gtc        402
Glu Ile Val Lys Ala Leu Leu Gly Lys Gly Ala Gln Val Asn Ala Val
             90                  95                 100 aat caa aat ggc tgt act ccc tta cat tat gca gct tcg aaa aac agg        450
Asn Gln Asn Gly Cys Thr Pro Leu His Tyr Ala Ala Ser Lys Asn Arg
        105                 110                 115 cat gag atc gct gtc atg tta ctg gaa ggc ggg gct aat cca gat gct        498
His Glu Ile Ala Val Met Leu Leu Glu Gly Gly Ala Asn Pro Asp Ala
    120                 125                 130 aag gac cat tat gag gct aca gca atg cac cgg gca gca gcc aag ggt        546
Lys Asp His Tyr Glu Ala Thr Ala Met His Arg Ala Ala Ala Lys Gly
135                 140                 145                 150 aac ttg aag atg att cat atc ctt ctg tac tac aaa gca tcc aca aac        594
```

```
                  Asn Leu Lys Met Ile His Ile Leu Leu Tyr Tyr Lys Ala Ser Thr Asn
                                  155                 160                 165 atc caa gac act gag ggt aac act cct cta cac tta gcc tgt gat gag           642
Ile Gln Asp Thr Glu Gly Asn Thr Pro Leu His Leu Ala Cys Asp Glu
                170                 175                 180 gag aga gtg gaa gaa gca aaa ctg ctg gtg tcc caa gga gca agt att           690
Glu Arg Val Glu Glu Ala Lys Leu Leu Val Ser Gln Gly Ala Ser Ile
            185                 190                 195 tac att gag aat aaa gaa gaa aag aca ccc ctg caa gtg gcc aaa ggt           738
Tyr Ile Glu Asn Lys Glu Glu Lys Thr Pro Leu Gln Val Ala Lys Gly
        200                 205                 210 ggc ctg ggt tta ata ctc aag aga atg gtg gaa ggt taaaca                    780
Gly Leu Gly Leu Ile Leu Lys Arg Met Val Glu Gly
215                 220                 225

<210> SEQ ID NO 2
<211> LENGTH: 226
<212> TYPE: PRT
<213> ORGANISM: Homo sapiens

<400> SEQUENCE: 2

Met Glu Gly Cys Val Ser Asn Leu Met Val Cys Asn Leu Ala Tyr Ser
 1               5                  10                  15

Gly Lys Leu Glu Glu Leu Lys Glu Ser Ile Leu Ala Asp Lys Ser Leu
            20                  25                  30

Ala Thr Arg Thr Asp Gln Asp Ser Arg Thr Ala Leu His Trp Ala Cys
        35                  40                  45

Ser Ala Gly His Thr Glu Ile Val Glu Phe Leu Leu Gln Leu Gly Val
    50                  55                  60

Pro Val Asn Asp Lys Asp Asp Ala Gly Trp Ser Pro Leu His Ile Ala
65                  70                  75                  80

Ala Ser Ala Gly Arg Asp Glu Ile Val Lys Ala Leu Leu Gly Lys Gly
                85                  90                  95

Ala Gln Val Asn Ala Val Asn Gln Asn Gly Cys Thr Pro Leu His Tyr
            100                 105                 110

Ala Ala Ser Lys Asn Arg His Glu Ile Ala Val Met Leu Leu Glu Gly
        115                 120                 125

Gly Ala Asn Pro Asp Ala Lys Asp His Tyr Glu Ala Thr Ala Met His
    130                 135                 140

Arg Ala Ala Ala Lys Gly Asn Leu Lys Met Ile His Ile Leu Leu Tyr
145                 150                 155                 160

Tyr Lys Ala Ser Thr Asn Ile Gln Asp Thr Glu Gly Asn Thr Pro Leu
                165                 170                 175

His Leu Ala Cys Asp Glu Glu Arg Val Glu Glu Ala Lys Leu Leu Val
            180                 185                 190

Ser Gln Gly Ala Ser Ile Tyr Ile Glu Asn Lys Glu Glu Lys Thr Pro
        195                 200                 205

Leu Gln Val Ala Lys Gly Gly Leu Gly Leu Ile Leu Lys Arg Met Val
    210                 215                 220

Glu Gly
225

<210> SEQ ID NO 3
<211> LENGTH: 696
<212> TYPE: DNA
<213> ORGANISM: Mus sp.
<220> FEATURE:
<221> NAME/KEY: CDS
```

<220> FEATURE:
<221> NAME/KEY: modified_base
<222> LOCATION: (198)
<223> OTHER INFORMATION: a, t, c or g

<400> SEQUENCE: 3

```
atg gag ggg tgt gtg tct aac ata atg atc tgt aac ctg gcc tac agt      48
Met Glu Gly Cys Val Ser Asn Ile Met Ile Cys Asn Leu Ala Tyr Ser
  1               5                  10                  15 ggg aag ctg gat gag ttg aag gag cgc att ttg gct gat aaa tct ctg      96
Gly Lys Leu Asp Glu Leu Lys Glu Arg Ile Leu Ala Asp Lys Ser Leu
             20                  25                  30 gct act aga act gat cag gac agc aga aca gct ttg cac tgg gca tgc     144
Ala Thr Arg Thr Asp Gln Asp Ser Arg Thr Ala Leu His Trp Ala Cys
         35                  40                  45 tca gct ggc cat aca gaa att gtt gaa ttc ttg ctg caa ctt gga gtg     192
Ser Ala Gly His Thr Glu Ile Val Glu Phe Leu Leu Gln Leu Gly Val
     50                  55                  60 cca gtn aat gat aaa gat gac gca ggt tgg tct cct ctt cat att gct     240
Pro Val Asn Asp Lys Asp Asp Ala Gly Trp Ser Pro Leu His Ile Ala
 65                  70                  75                  80 gcc tcc gct ggc cgg gat gag att gta aaa gcc ctt ctg gtg aaa ggt     288
Ala Ser Ala Gly Arg Asp Glu Ile Val Lys Ala Leu Leu Val Lys Gly
                 85                  90                  95 gca cat gtt aat tct gtc aat caa aac ggc tgc act cca ctc cat tat     336
Ala His Val Asn Ser Val Asn Gln Asn Gly Cys Thr Pro Leu His Tyr
            100                 105                 110 gca gct tcg aag aat agg cat gag att tct gtt atg tta cta gaa ggt     384
Ala Ala Ser Lys Asn Arg His Glu Ile Ser Val Met Leu Leu Glu Gly
        115                 120                 125 ggg gct aac cca gat gcg aag gac cat tac gat gct aca gca atg cac     432
Gly Ala Asn Pro Asp Ala Lys Asp His Tyr Asp Ala Thr Ala Met His
    130                 135                 140 cgg gca gca gcc aag ggt aac ttg aag atg gtt cac atc ctt ctg ttc     480
Arg Ala Ala Ala Lys Gly Asn Leu Lys Met Val His Ile Leu Leu Phe
145                 150                 155                 160 tac aaa gca tcc aca aac atc caa gac act gag ggt aac act cct cta     528
Tyr Lys Ala Ser Thr Asn Ile Gln Asp Thr Glu Gly Asn Thr Pro Leu
                165                 170                 175 cac tta gcc tgt gat gaa gag aga gtg gaa gag gca aaa ttt ctg gtg     576
His Leu Ala Cys Asp Glu Glu Arg Val Glu Glu Ala Lys Phe Leu Val
            180                 185                 190 act caa gga gca agt att tac att gag aat aaa gaa gaa aag aca ccc     624
Thr Gln Gly Ala Ser Ile Tyr Ile Glu Asn Lys Glu Glu Lys Thr Pro
        195                 200                 205 ctg caa gtt gcc aaa ggg ggc ctg ggt tta ata ctc aag aga cta gca     672
Leu Gln Val Ala Lys Gly Gly Leu Gly Leu Ile Leu Lys Arg Leu Ala
    210                 215                 220 gaa agt gaa gag gct tct atg tag                                     696
Glu Ser Glu Glu Ala Ser Met
225                 230
```

<210> SEQ ID NO 4
<211> LENGTH: 231
<212> TYPE: PRT
<213> ORGANISM: Mus sp.

<400> SEQUENCE: 4

```
Met Glu Gly Cys Val Ser Asn Ile Met Ile Cys Asn Leu Ala Tyr Ser
  1               5                  10                  15
```

```
Gly Lys Leu Asp Glu Leu Lys Glu Arg Ile Leu Ala Asp Lys Ser Leu
             20                  25                  30

Ala Thr Arg Thr Asp Gln Asp Ser Arg Thr Ala Leu His Trp Ala Cys
         35                  40                  45

Ser Ala Gly His Thr Glu Ile Val Glu Phe Leu Gln Leu Gly Val
     50                  55                  60

Pro Val Asn Asp Lys Asp Asp Ala Gly Trp Ser Pro Leu His Ile Ala
 65                  70                  75                  80

Ala Ser Ala Gly Arg Asp Glu Ile Val Lys Ala Leu Leu Val Lys Gly
                 85                  90                  95

Ala His Val Asn Ser Val Asn Gln Asn Gly Cys Thr Pro Leu His Tyr
            100                 105                 110

Ala Ala Ser Lys Asn Arg His Glu Ile Ser Val Met Leu Leu Glu Gly
            115                 120                 125

Gly Ala Asn Pro Asp Ala Lys Asp His Tyr Asp Ala Thr Ala Met His
        130                 135                 140

Arg Ala Ala Lys Gly Asn Leu Lys Met Val His Ile Leu Leu Phe
145                 150                 155                 160

Tyr Lys Ala Ser Thr Asn Ile Gln Asp Thr Glu Gly Asn Thr Pro Leu
                165                 170                 175

His Leu Ala Cys Asp Glu Glu Arg Val Glu Glu Ala Lys Phe Leu Val
            180                 185                 190

Thr Gln Gly Ala Ser Ile Tyr Ile Glu Asn Lys Glu Lys Thr Pro
        195                 200                 205

Leu Gln Val Ala Lys Gly Gly Leu Gly Leu Ile Leu Lys Arg Leu Ala
    210                 215                 220

Glu Ser Glu Glu Ala Ser Met
225                 230

<210> SEQ ID NO 5
<211> LENGTH: 696
<212> TYPE: DNA
<213> ORGANISM: Rattus sp.
<220> FEATURE:
<221> NAME/KEY: CDS
<222> LOCATION: (1)..(693)

<400> SEQUENCE: 5 atg gag ggg tgt gtg tct aac cta atg gtc tgt aac ctg gcc tac aac    48
Met Glu Gly Cys Val Ser Asn Leu Met Val Cys Asn Leu Ala Tyr Asn
 1               5                  10                  15 ggg aag ctg gat gag ttg aag gaa agc att ttg gct gat aag tct ctg    96
Gly Lys Leu Asp Glu Leu Lys Glu Ser Ile Leu Ala Asp Lys Ser Leu
             20                  25                  30 gcc act aga act gat cag gac agc aga aca gca ttg cac tgg gca tgc   144
Ala Thr Arg Thr Asp Gln Asp Ser Arg Thr Ala Leu His Trp Ala Cys
         35                  40                  45 tca gct ggt cat aca gaa att gtt gaa ttc ttg ctg caa ctt gga gtg   192
Ser Ala Gly His Thr Glu Ile Val Glu Phe Leu Leu Gln Leu Gly Val
     50                  55                  60 cca gta aat gaa aaa gac gat gca ggt tgg tct cct ctt cat att gct   240
Pro Val Asn Glu Lys Asp Asp Ala Gly Trp Ser Pro Leu His Ile Ala
 65                  70                  75                  80 gct tcc gct ggc cgg gat gag att gta aaa gcc ctt ctg ata aaa ggg   288
Ala Ser Ala Gly Arg Asp Glu Ile Val Lys Ala Leu Leu Ile Lys Gly
                 85                  90                  95 gca caa gtg aat gcc gtc aat cag aat ggc tgc acg gcc ctt cat tat   336
Ala Gln Val Asn Ala Val Asn Gln Asn Gly Cys Thr Ala Leu His Tyr
            100                 105                 110
```

-continued

```
              100                 105                 110
gca gct tcc aag aat agg cat gag att gct gtt atg tta cta gaa ggt    384
Ala Ala Ser Lys Asn Arg His Glu Ile Ala Val Met Leu Leu Glu Gly
        115                 120                 125 ggg gct aat cca gat gct aag aac cat tat gat gct aca gca atg cac    432
Gly Ala Asn Pro Asp Ala Lys Asn His Tyr Asp Ala Thr Ala Met His
130                 135                 140 cgg gca gca gcc aag ggt aac ttg aag atg gtt cat atc ctt ctg ttc    480
Arg Ala Ala Ala Lys Gly Asn Leu Lys Met Val His Ile Leu Leu Phe
145                 150                 155                 160 tac aaa gca tcc aca aac atc caa gat act gag ggt aac act cct cta    528
Tyr Lys Ala Ser Thr Asn Ile Gln Asp Thr Glu Gly Asn Thr Pro Leu
                165                 170                 175 cac tta gcc tgt gat gag gag aga gtg gaa gaa gca aaa ttg ctg gtg    576
His Leu Ala Cys Asp Glu Glu Arg Val Glu Glu Ala Lys Leu Leu Val
            180                 185                 190 acc caa gga gca agt att tac att gaa aat aag gaa gaa aag aca ccg    624
Thr Gln Gly Ala Ser Ile Tyr Ile Glu Asn Lys Glu Glu Lys Thr Pro
        195                 200                 205 ctg caa gtc gcc aaa ggg ggc ctg ggt tta ata ctc aaa aga atc gca    672
Leu Gln Val Ala Lys Gly Gly Leu Gly Leu Ile Leu Lys Arg Ile Ala
    210                 215                 220 gaa agt gaa gag gct tct atg tag                                    696
Glu Ser Glu Glu Ala Ser Met
225                 230

<210> SEQ ID NO 6
<211> LENGTH: 231
<212> TYPE: PRT
<213> ORGANISM: Rattus sp.

<400> SEQUENCE: 6

Met Glu Gly Cys Val Ser Asn Leu Met Val Cys Asn Leu Ala Tyr Asn
 1               5                  10                  15

Gly Lys Leu Asp Glu Leu Lys Glu Ser Ile Leu Ala Asp Lys Ser Leu
            20                  25                  30

Ala Thr Arg Thr Asp Gln Asp Ser Arg Thr Ala Leu His Trp Ala Cys
        35                  40                  45

Ser Ala Gly His Thr Glu Ile Val Glu Phe Leu Leu Gln Leu Gly Val
    50                  55                  60

Pro Val Asn Glu Lys Asp Asp Ala Gly Trp Ser Pro Leu His Ile Ala
65                  70                  75                  80

Ala Ser Ala Gly Arg Asp Glu Ile Val Lys Ala Leu Leu Ile Lys Gly
                85                  90                  95

Ala Gln Val Asn Ala Val Asn Gln Asn Gly Cys Thr Ala Leu His Tyr
            100                 105                 110

Ala Ala Ser Lys Asn Arg His Glu Ile Ala Val Met Leu Leu Glu Gly
        115                 120                 125

Gly Ala Asn Pro Asp Ala Lys Asn His Tyr Asp Ala Thr Ala Met His
    130                 135                 140

Arg Ala Ala Ala Lys Gly Asn Leu Lys Met Val His Ile Leu Leu Phe
145                 150                 155                 160

Tyr Lys Ala Ser Thr Asn Ile Gln Asp Thr Glu Gly Asn Thr Pro Leu
                165                 170                 175

His Leu Ala Cys Asp Glu Glu Arg Val Glu Glu Ala Lys Leu Leu Val
            180                 185                 190

Thr Gln Gly Ala Ser Ile Tyr Ile Glu Asn Lys Glu Glu Lys Thr Pro
```

-continued

```
                    195                 200                 205
Leu Gln Val Ala Lys Gly Gly Leu Gly Leu Ile Leu Lys Arg Ile Ala
    210                 215                 220

Glu Ser Glu Glu Ala Ser Met
225                 230

<210> SEQ ID NO 7
<211> LENGTH: 15
<212> TYPE: PRT
<213> ORGANISM: Homo sapiens

<400> SEQUENCE: 7

Met Glu Gly Cys Val Ser Asn Leu Met Val Cys Asn Leu Ala Tyr
  1               5                  10                  15

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
acccctccat ttcgctgtcc                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
ttagacacac acccctccat                                                  20

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: ANK
      consensus
<220> FEATURE:
<221> NAME/KEY: MOD_RES
<222> LOCATION: (3)
<223> OTHER INFORMATION: P or A
<220> FEATURE:
<221> NAME/KEY: MOD_RES
<222> LOCATION: (6)
<223> OTHER INFORMATION: L, I or V
<220> FEATURE:
<221> NAME/KEY: MOD_RES
<222> LOCATION: (8)
<223> OTHER INFORMATION: A or S
<220> FEATURE:
<221> NAME/KEY: MOD_RES
<222> LOCATION: (9)
<223> OTHER INFORMATION: R, Q or K
<220> FEATURE:
<221> NAME/KEY: MOD_RES
<222> LOCATION: (10)
<223> OTHER INFORMATION: G or N
<220> FEATURE:
<221> NAME/KEY: MOD_RES
<222> LOCATION: (11)
<223> OTHER INFORMATION: H or N
<220> FEATURE:
<221> NAME/KEY: MOD_RES
```

```
<222> LOCATION: (12)
<223> OTHER INFORMATION: V, L or T
<220> FEATURE:
<221> NAME/KEY: MOD_RES
<222> LOCATION: (13)
<223> OTHER INFORMATION: E or D
<220> FEATURE:
<221> NAME/KEY: MOD_RES
<222> LOCATION: (14)
<223> OTHER INFORMATION: V, I or M
<220> FEATURE:
<221> NAME/KEY: MOD_RES
<222> LOCATION: (15)
<223> OTHER INFORMATION: V or A
<220> FEATURE:
<221> NAME/KEY: MOD_RES
<222> LOCATION: (16)
<223> OTHER INFORMATION: K, E or R
<220> FEATURE:
<221> NAME/KEY: MOD_RES
<222> LOCATION: (17)
<223> OTHER INFORMATION: L or V
<220> FEATURE:
<221> NAME/KEY: MOD_RES
<222> LOCATION: (20)
<223> OTHER INFORMATION: D, K, Q or E
<220> FEATURE:
<221> NAME/KEY: MOD_RES
<222> LOCATION: (23)
<223> OTHER INFORMATION: D, N or S
<220> FEATURE:
<221> NAME/KEY: MOD_RES
<222> LOCATION: (24)
<223> OTHER INFORMATION: V, P or I
<220> FEATURE:
<221> NAME/KEY: MOD_RES
<222> LOCATION: (25)
<223> OTHER INFORMATION: N or D
<220> FEATURE:
<221> NAME/KEY: MOD_RES
<222> LOCATION: (27)
<223> OTHER INFORMATION: T, D or N

<400> SEQUENCE: 10

Gly Thr Xaa Leu His Xaa Ala Xaa Xaa Xaa Xaa Xaa Xaa Xaa Xaa
  1               5                  10                  15

Xaa Leu Leu Xaa Gly Ala Xaa Xaa Xaa Ala Xaa Lys
                20                  25

<210> SEQ ID NO 11
<211> LENGTH: 33
<212> TYPE: PRT
<213> ORGANISM: Homo sapiens
<220> FEATURE:
<223> OTHER INFORMATION: ankyrin repeat

<400> SEQUENCE: 11

Asp Ser Arg Thr Ala Leu His Trp Ala Cys Ser Ala Gly His Thr Glu
  1               5                  10                  15

Ile Val Glu Phe Leu Leu Gln Leu Gly Val Pro Val Asn Asp Lys Asp
                20                  25                  30

Asp

<210> SEQ ID NO 12
<211> LENGTH: 33
<212> TYPE: PRT
<213> ORGANISM: Homo sapiens
<220> FEATURE:
<223> OTHER INFORMATION: ankyrin repeat

<400> SEQUENCE: 12
```

```
Ala Gly Trp Ser Pro Leu His Ile Ala Ala Ser Ala Gly Arg Asp Glu
  1               5                  10                  15

Ile Val Lys Ala Leu Leu Gly Lys Gly Ala Gln Val Asn Ala Val Asn
                 20                  25                  30

Gln
```

<210> SEQ ID NO 13
<211> LENGTH: 33
<212> TYPE: PRT
<213> ORGANISM: Homo sapiens
<220> FEATURE:
<223> OTHER INFORMATION: ankyrin repeat

<400> SEQUENCE: 13

```
Asn Gly Cys Thr Pro Leu His Tyr Ala Ala Ser Lys Asn Arg His Glu
  1               5                  10                  15

Ile Ala Val Met Leu Leu Glu Gly Gly Ala Asn Pro Asp Ala Lys Asp
                 20                  25                  30

His
```

<210> SEQ ID NO 14
<211> LENGTH: 33
<212> TYPE: PRT
<213> ORGANISM: Homo sapiens
<220> FEATURE:
<223> OTHER INFORMATION: ankyrin repeat

<400> SEQUENCE: 14

```
Tyr Glu Ala Thr Ala Met His Arg Ala Ala Ala Lys Gly Asn Leu Lys
  1               5                  10                  15

Met Ile His Ile Leu Leu Tyr Tyr Lys Ala Ser Thr Asn Ile Gln Asp
                 20                  25                  30

Thr
```

<210> SEQ ID NO 15
<211> LENGTH: 33
<212> TYPE: PRT
<213> ORGANISM: Homo sapiens
<220> FEATURE:
<223> OTHER INFORMATION: ankyrin repeat

<400> SEQUENCE: 15

```
Glu Gly Asn Thr Pro Leu His Leu Ala Cys Asp Glu Glu Arg Val Glu
  1               5                  10                  15

Glu Ala Lys Leu Leu Val Ser Gln Gly Ala Ser Ile Tyr Ile Glu Asn
                 20                  25                  30

Lys
```

<210> SEQ ID NO 16
<211> LENGTH: 23
<212> TYPE: PRT
<213> ORGANISM: Homo sapiens
<220> FEATURE:
<223> OTHER INFORMATION: ankyrin repeat

<400> SEQUENCE: 16

```
Glu Glu Lys Thr Pro Leu Gln Val Ala Lys Gly Gly Leu Gly Leu Ile
  1               5                  10                  15

Leu Lys Arg Met Val Glu Gly
                 20
```